(12) United States Patent
Jamieson et al.

(10) Patent No.: US 9,194,862 B2
(45) Date of Patent: Nov. 24, 2015

(54) COMPOSITIONS AND METHODS FOR DETERMINING CANCER STEM CELL SELF-RENEWAL POTENTIAL

(75) Inventors: Catriona H. Jamieson, La Jolla, CA (US); Annelie Schairer, Escondido, CA (US); Ifat Geron, San Diego, CA (US); Kim-Hien Dao, Portland, OR (US); Daniel Jacob Goff, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 291 days.

(21) Appl. No.: 12/821,738

(22) Filed: Jun. 23, 2010

(65) Prior Publication Data

US 2011/0059448 A1 Mar. 10, 2011

Related U.S. Application Data

(60) Provisional application No. 61/219,685, filed on Jun. 23, 2009, provisional application No. 61/219,702, filed on Jun. 23, 2009.

(51) Int. Cl.
| | |
|---|---|
| *C12Q 1/00* | (2006.01) |
| *C12Q 1/02* | (2006.01) |
| *G01N 33/50* | (2006.01) |
| *C12Q 1/68* | (2006.01) |

(52) U.S. Cl.
CPC .......... *G01N 33/5011* (2013.01); *C12Q 1/6883* (2013.01); *C12Q 1/6886* (2013.01); *G01N 33/5073* (2013.01); *C12Q 2600/106* (2013.01); *C12Q 2600/156* (2013.01); *C12Q 2600/158* (2013.01); *G01N 2800/50* (2013.01)

(58) Field of Classification Search
None
See application file for complete search history.

(56) References Cited

U.S. PATENT DOCUMENTS 7,217,568 B2 * 5/2007 Jamieson et al. ............. 435/375

FOREIGN PATENT DOCUMENTS

WO WO2006/136951 * 12/2006

OTHER PUBLICATIONS

The abstract of Konopleva et al (Blood, 1998, vol. 92, 10 suppl. 1, part 1-2, pp. 600-601A).*
Jamieson et al (Cancer Cell, 2004 vol. 6, pp. 531-533).*
Lunghi et al (Haematologica Reports, 2005, vol. 1, pp. 32-35).*
Visvader and Lindeman (Nature Reviews Cancer, 2008, vol. 8, pp. 755-767).*
Goff et al (Blood, Nov. 2008, vol. 112, No. 11, p. 393).*
Robinson, PLoS Biology, 2004, vol. 1, pp. 0018-0020.*
ClinicalTrials.gov Archive (NCT00049192, Jun. 23, 2005).*
Chiu et al (Journal of Controlled Release, 2006, vol. 112, pp. 199-207).*
Meng et al (Leukemia and Lymphoma, 2007, vol. 48, pp. 2204-2212).*
Pellecchia and Reed (Current Pharmaceutical Design, 2004, vol. 10, pp. 1387-1398).*
ATCC Catalog No. CCL-243, downloaded Apr. 24, 2015.*
Marques et al (Leukemia Research, vol. 34, pp. 757-762).*

* cited by examiner

*Primary Examiner* — Karen Canella
(74) *Attorney, Agent, or Firm* — Gregory P. Einhorn; Greer Burns & Crain Ltd.

(57) ABSTRACT

In alternative embodiments, the invention provides compositions and methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC, the method comprising detecting and quantifying in CSCs one or more B-cell lymphoma-2 (Bcl-2) family protein isoform(s) or transcripts (mRNAs, messages) encoding one or more Bcl-2 family protein(s) or protein isoform(s) thereof. In alternative embodiments, the invention provides compositions and methods to determine and measure the levels of Wnt, glycogen synthase kinase-3 beta (GSK-3 beta), glycogen synthase kinase-3 alpha (GSK-3 alpha), and/or Sonic Hedgehog Homolog (SHH or Shh) family proteins and alternatively spliced transcripts (mRNAs), and Wnt, GSK3beta, GSK3alpha and/or Shh family protein and alternatively spliced transcript ratios in cancer cells, e.g., stem cells, e.g., CSCs, for diagnostic, drug discovery and prognostic purposes.

1 Claim, 26 Drawing Sheets

FIG. 3C (Con't)

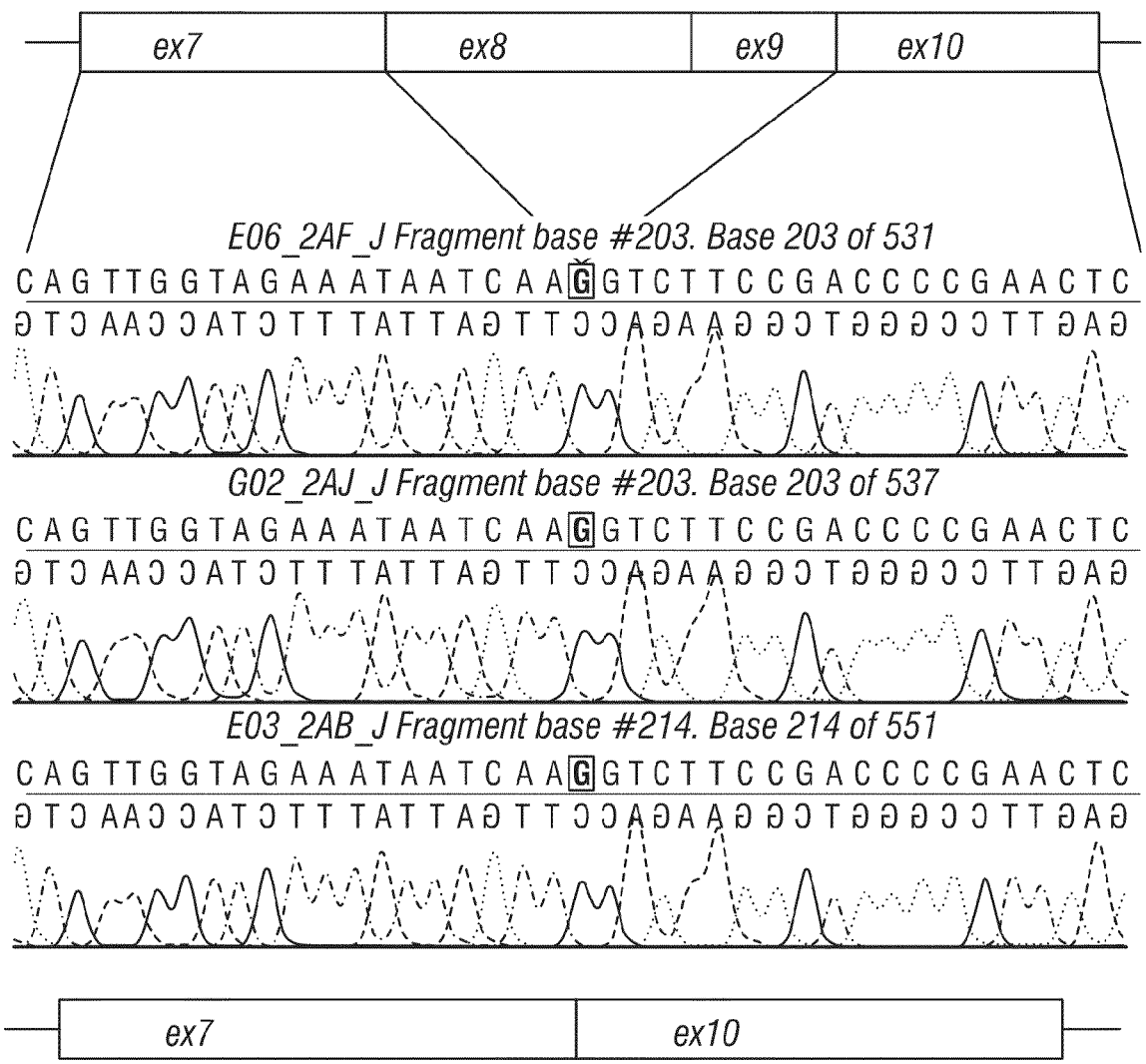
FIG. 9 (Con't)

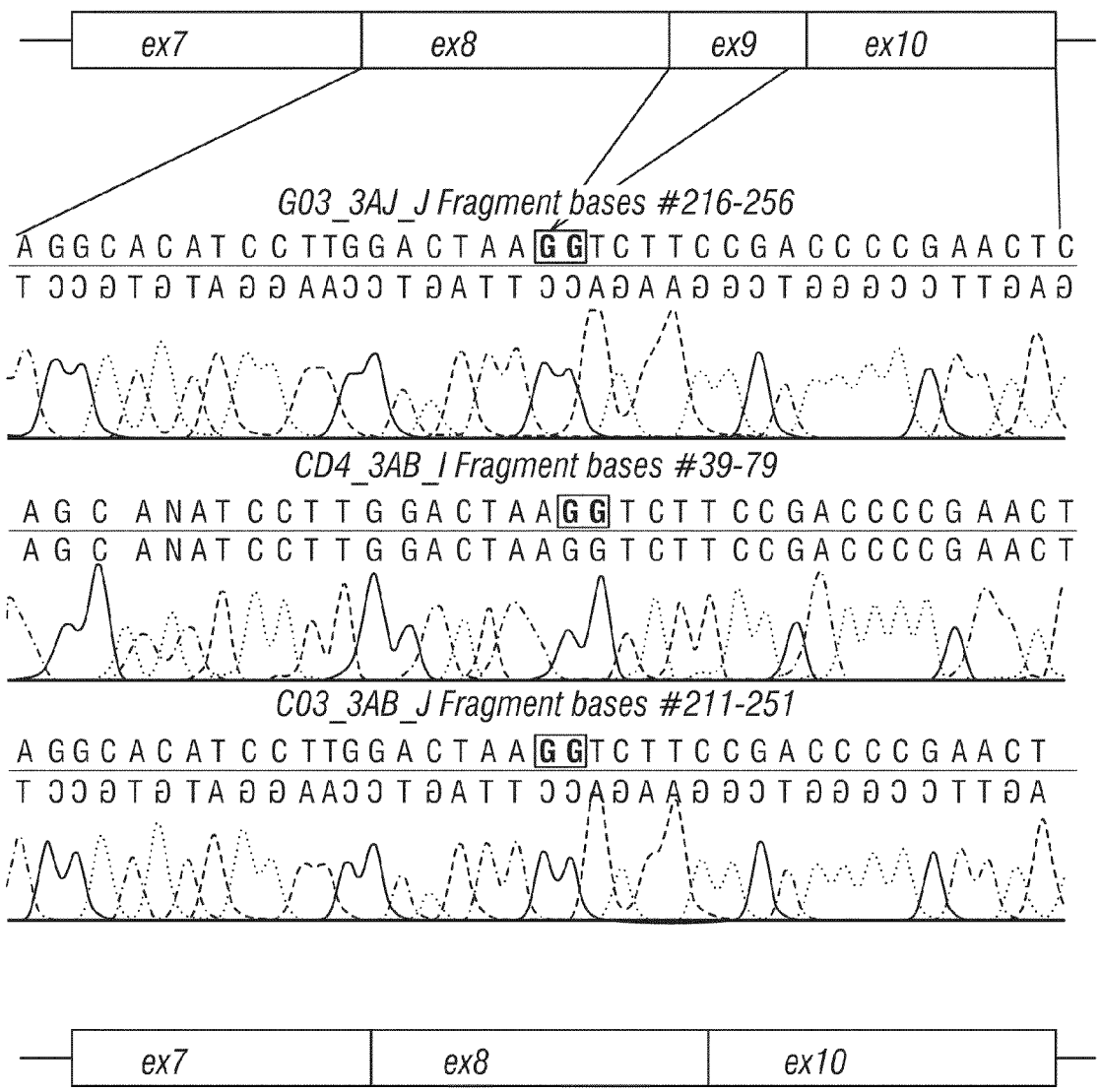
FIG. 9 (Con't)

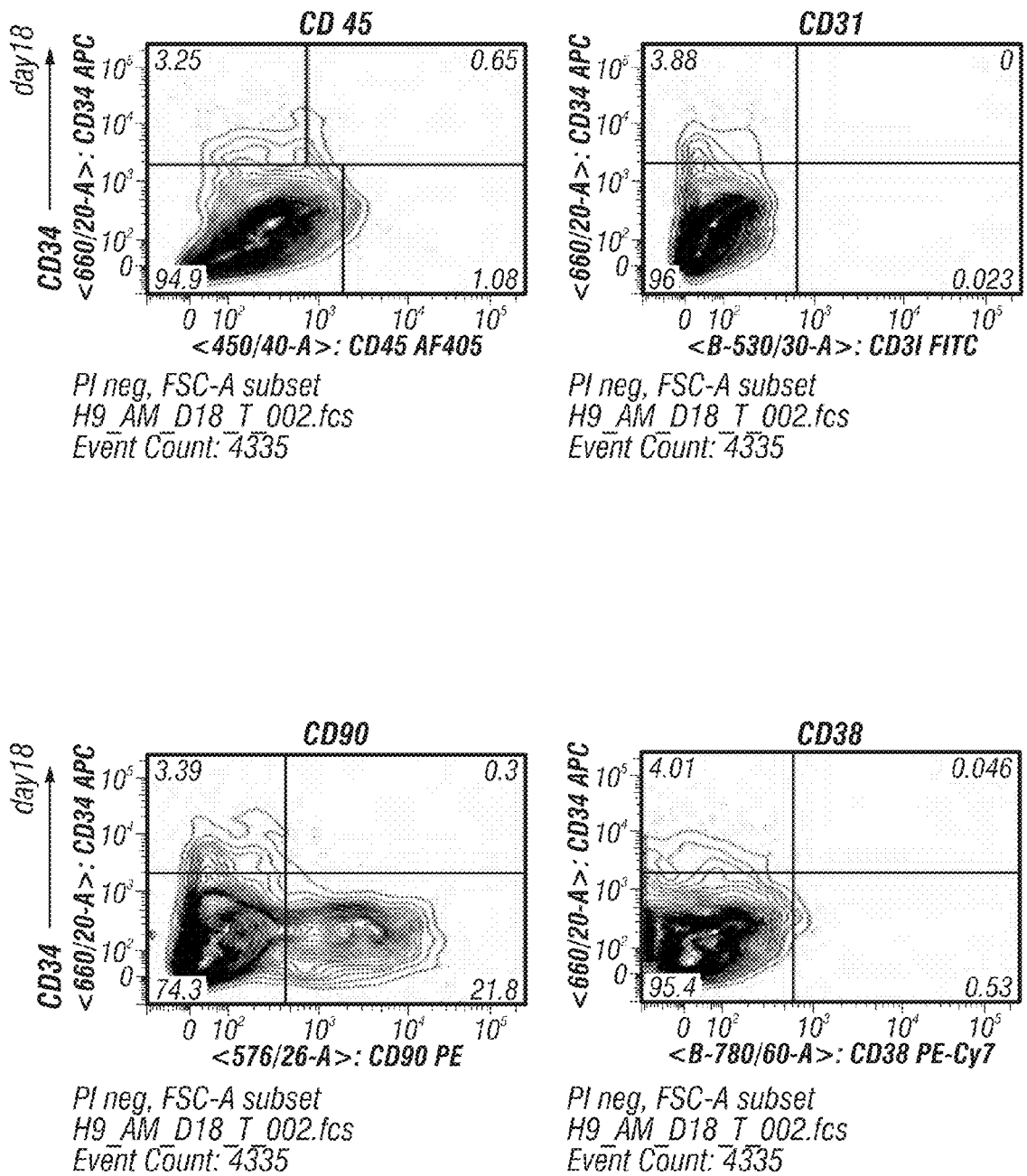
FIG. 15 (Con't)

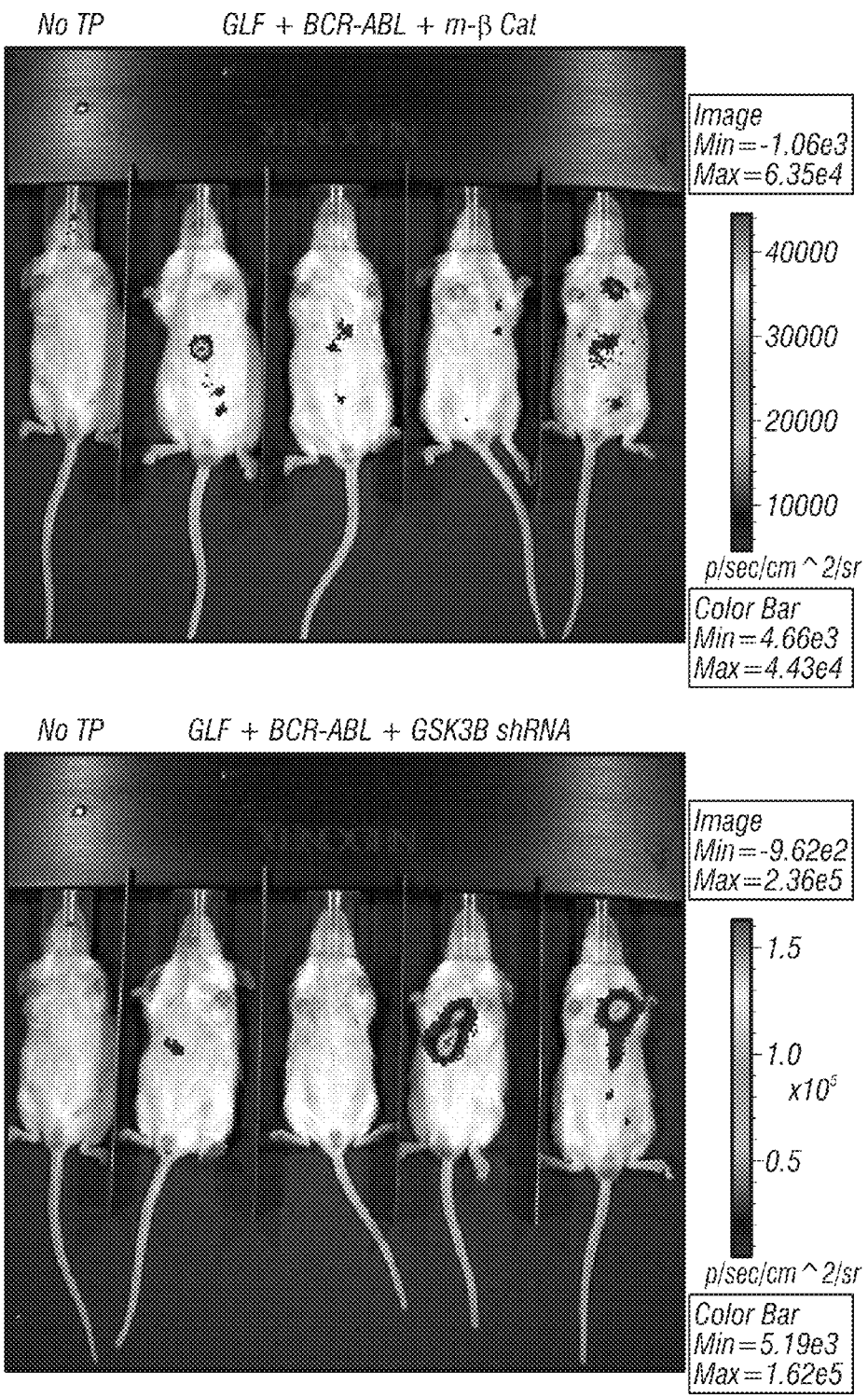
FIG. 15 (Con't)

SEQUENCE LISTING

```
<160> NUMBER OF SEQ ID NOS: 20

<210> SEQ ID NO 1
<211> LENGTH: 37
<212> TYPE: DNA
<213> ORGANISM: Homo sapiens
<220> FEATURE:
<221> NAME/KEY: misc_feature
<222> LOCATION: (1)..(1)
<223> OTHER INFORMATION: wherein N is any base
<220> FEATURE:
<221> NAME/KEY: misc_feature
<222> LOCATION: (3)..(5)
<223> OTHER INFORMATION: wherein N is any base
<220> FEATURE:
<221> NAME/KEY: misc_feature
<222> LOCATION: (7)..(11)
<223> OTHER INFORMATION: wherein N is any base

<400> SEQUENCE: 1
nannngnnnn natcaaggtc ttccgacccc gaactcc                              37

<210> SEQ ID NO 2
<211> LENGTH: 37
<212> TYPE: DNA
<213> ORGANISM: Homo sapiens
<220> FEATURE:
<221> NAME/KEY: misc_feature
```

```
<222> LOCATION: (26)..(31)
<223> OTHER INFORMATION: wherein N is any base
<220> FEATURE:
<221> NAME/KEY: misc_feature
<222> LOCATION: (33)..(35)
<223> OTHER INFORMATION: wherein N is any base
<220> FEATURE:
<221> NAME/KEY: misc_feature
<222> LOCATION: (37)..(37)
<223> OTHER INFORMATION: wherein N is any base

<400> SEQUENCE: 2
ggagttcggg gtcggaagac cttgatnnnn ncnnntn                              37

<210> SEQ ID NO 3
<211> LENGTH: 37
<212> TYPE: DNA
<213> ORGANISM: Homo sapiens
<220> FEATURE:
<221> NAME/KEY: misc_feature
<222> LOCATION: (2)..(2)
<223> OTHER INFORMATION: wherein N is any base
<220> FEATURE:
<221> NAME/KEY: misc_feature
<222> LOCATION: (4)..(4)
<223> OTHER INFORMATION: wherein N is any base
<220> FEATURE:
<221> NAME/KEY: misc_feature
<222> LOCATION: (6)..(7)
<223> OTHER INFORMATION: wherein N is any base
<220> FEATURE:
<221> NAME/KEY: misc_feature
<222> LOCATION: (10)..(11)
<223> OTHER INFORMATION: wherein N is any base

<400> SEQUENCE: 3
cncntnnaan natcaaggtc ttccgacccc gaactcc                              37

<210> SEQ ID NO 4
<211> LENGTH: 37
<212> TYPE: DNA
<213> ORGANISM: Homo sapiens
<220> FEATURE:
<221> NAME/KEY: misc_feature
<222> LOCATION: (27)..(28)
<223> OTHER INFORMATION: wherein N is any base
<220> FEATURE:
<221> NAME/KEY: misc_feature
<222> LOCATION: (31)..(32)
<223> OTHER INFORMATION: wherein N is any base
<220> FEATURE:
<221> NAME/KEY: misc_feature
<222> LOCATION: (34)..(34)
<223> OTHER INFORMATION: wherein N is any base
<220> FEATURE:
<221> NAME/KEY: misc_feature
<222> LOCATION: (36)..(36)
<223> OTHER INFORMATION: wherein N is any base

<400> SEQUENCE: 4
ggagttcggg gtcggaagac cttgatnnttt nnangng                             37

<210> SEQ ID NO 5
<211> LENGTH: 37
<212> TYPE: DNA
<213> ORGANISM: Homo sapiens
<220> FEATURE:
<221> NAME/KEY: misc_feature
<222> LOCATION: (5)..(7)
<223> OTHER INFORMATION: wherein N is any base
<220> FEATURE:
<221> NAME/KEY: misc_feature
<222> LOCATION: (11)..(11)
```

```
<223> OTHER INFORMATION: wherein N is any base
<220> FEATURE:
<221> NAME/KEY: misc_feature
<222> LOCATION: (13)..(13)
<223> OTHER INFORMATION: wherein N is any base

<400> SEQUENCE: 5 gcagnnaat nantaaggtc ttccgacccc gaactcc                              37

<210> SEQ ID NO 6
<211> LENGTH: 37
<212> TYPE: DNA
<213> ORGANISM: Homo sapiens
<220> FEATURE:
<221> NAME/KEY: misc_feature
<222> LOCATION: (25)..(25)
<223> OTHER INFORMATION: wherein N is any base
<220> FEATURE:
<221> NAME/KEY: misc_feature
<222> LOCATION: (27)..(27)
<223> OTHER INFORMATION: wherein N is any base
<220> FEATURE:
<221> NAME/KEY: misc_feature
<222> LOCATION: (31)..(33)
<223> OTHER INFORMATION: wherein N is any base

<400> SEQUENCE: 6
ggagttcggg gtcggaagac cttantnatt nnnctgc                             37

<210> SEQ ID NO 7
<211> LENGTH: 37
<212> TYPE: DNA
<213> ORGANISM: Homo sapiens
<220> FEATURE:
<221> NAME/KEY: misc_feature
<222> LOCATION: (2)..(2)
<223> OTHER INFORMATION: wherein N is any base
<220> FEATURE:
<221> NAME/KEY: misc_feature
<222> LOCATION: (4)..(4)
<223> OTHER INFORMATION: wherein N is any base
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(1)
<223> OTHER INFORMATION: wherein N is any base
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (14)..(14)
<223> OTHER INFORMATION: wherein N is any base

<400> SEQUENCE: 7
cncntcnaan natnaaggtc ttccgacccc gaactcc                             37

<210> SEQ ID NO 8
<211> LENGTH: 37
<212> TYPE: DNA
<213> ORGANISM: Homo sapiens
<220> FEATURE:
<221> NAME/KEY: misc_feature
<222> LOCATION: (24)..(24)
<223> OTHER INFORMATION: wherein N is any base
<220> FEATURE:
<221> NAME/KEY: misc_feature
<222> LOCATION: (27)..(28)
<223> OTHER INFORMATION: wherein N is any base
```

```
<220> FEATURE:
<221> NAME/KEY: misc_feature
<222> LOCATION: (31)..(31)
<223> OTHER INFORMATION: wherein N is any base
<220> FEATURE:
<221> NAME/KEY: misc_feature
<222> LOCATION: (34)..(34)
<223> OTHER INFORMATION: wherein N is any base
<220> FEATURE:
<221> NAME/KEY: misc_feature
<222> LOCATION: (36)..(36)
<223> OTHER INFORMATION: wherein N is any base

<400> SEQUENCE: 8
ggagttcggg gtcggaagac cttnatnntt ngangng                              37

<210> SEQ ID NO 9
<211> LENGTH: 37
<212> TYPE: DNA
<213> ORGANISM: Homo sapiens

<400> SEQUENCE: 9
cagttgtaga aataataagg tcttccgacc cgaactc                              37

<210> SEQ ID NO 10
<211> LENGTH: 37
<212> TYPE: DNA
<213> ORGANISM: Homo sapiens

<400> SEQUENCE: 10
gagttccggt cggaagacct tattatttct acaactg                              37

<210> SEQ ID NO 11
<211> LENGTH: 37
<212> TYPE: DNA
<213> ORGANISM: Homo sapiens

<400> SEQUENCE: 11
cagttgtaga aataataagg tcttccgacc cgaactc                              37

<210> SEQ ID NO 12
<211> LENGTH: 37
<212> TYPE: DNA
<213> ORGANISM: Homo sapiens

<400> SEQUENCE: 12
gagttccggt cggaagacct tattatttct acaactg                              37

<210> SEQ ID NO 13
<211> LENGTH: 37
<212> TYPE: DNA
<213> ORGANISM: Homo sapiens

<400> SEQUENCE: 13
cagttgtaga aataataagg tcttccgacc cgaactc                              37

<210> SEQ ID NO 14
<211> LENGTH: 37
<212> TYPE: DNA
<213> ORGANISM: Homo sapiens

<400> SEQUENCE: 14
gagttccggt cggaagacct tattatttct acaactg                              37

<210> SEQ ID NO 15
```

```
<211> LENGTH: 36
<212> TYPE: DNA
<213> ORGANISM: Homo sapiens

<400> SEQUENCE: 15
aggccatcct tggacaaggt cttccgaccc gaactc                               36

<210> SEQ ID NO 16
<211> LENGTH: 36
<212> TYPE: DNA
<213> ORGANISM: Homo sapiens

<400> SEQUENCE: 16
gagttccggt cggaagacct tgtccaagga tggcct                               36

<210> SEQ ID NO 17
<211> LENGTH: 37
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 17
agcanatcct tggactaagg tcttccgacc ccgaact                              37

<210> SEQ ID NO 18
<211> LENGTH: 37
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 18
agcanatcct tggactaagg tcttccgacc ccgaact                              37

<210> SEQ ID NO 19
<211> LENGTH: 35
<212> TYPE: DNA
<213> ORGANISM: Homo sapiens

<400> SEQUENCE: 19
aggccatcct tggacaaggt cttccgaccc gaact                                35

<210> SEQ ID NO 20
<211> LENGTH: 35
<212> TYPE: DNA
<213> ORGANISM: Homo sapiens

<400> SEQUENCE: 20
agttccggtc ggaagacctt gtccaaggat ggcct                                35
```

COMPOSITIONS AND METHODS FOR DETERMINING CANCER STEM CELL SELF-RENEWAL POTENTIAL

RELATED APPLICATIONS

This application is a claims the benefit of priority under 35 U.S.C. §119(e) of U.S. Provisional Patent Application Ser. No. 61/219,685, filed Jun. 23, 2010, and U.S. Ser. No. 61/219,702, filed Jun. 23, 2010. Each of the aforementioned applications are expressly incorporated herein by reference in their entirety and for all purposes.

TECHNICAL FIELD

This invention relates to cellular and developmental biology, drug discovery and oncology. In alternative embodiments, the invention provides compositions and methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC, the method comprising detecting and quantifying in CSCs one or more B-cell lymphoma-2 (Bcl-2) family protein isoform(s) or transcripts (mRNAs, messages) encoding one or more Bcl-2 family protein(s) or protein isoform(s) thereof. In alternative embodiments, the invention provides compositions and methods to determine and measure the levels of Wnt, glycogen synthase kinase-3 beta (GSK-3 beta), glycogen synthase kinase-3 alpha (GSK-3 alpha), and/or Sonic Hedgehog Homolog (SHH or Shh) family proteins and alternatively spliced transcripts (mRNAs), and Wnt, GSK3beta, GSK3alpha and/or Shh family protein and alternatively spliced transcript ratios in cancer cells, e.g., stem cells, e.g., CSCs, for diagnostic, drug discovery and prognostic purposes.

BACKGROUND

A growing body of evidence suggests that a relatively rare subset of cells within a cancer subverts properties normally ascribed to stem cells in regenerating tissues, such as enhanced self-renewal and survival capacity. Recent studies suggest that these cancer stem cells (CSC) are resistant to treatments that target rapidly dividing cells. Recent studies suggest that in blast crisis chronic myeloid leukemia (BC CML) and some forms of acute myeloid leukemia (AML) CSC originate from the $CD34^+CD38^+lineage^-$ compartment of hematopoietic cells and can serially transplant blast crisis leukemia in immunodeficient mice.

Unlike stem cells in regenerating tissues, which are characterized by enhanced self-renewal and survival capacity, recent studies suggests that cancer stem cells (CSC) are resistant to treatments that target rapidly dividing cells.

With progression to blast crisis, CML stem cells become more resistant to therapies targeting BCR-ABL. As BCR-ABL targeted therapy initiates apoptosis, these results suggest that CML CSC may become increasingly resistant to apoptosis with progression.

Existing methods for predicting leukemia progression and drug susceptibility analyze the bulk of cells from a leukemia and do not quantitate Bcl-2 family molecules. However, not all cells in a leukemia are equivalent and CSCs in particular display aberrant expression of Bcl-2 molecules. Because CSCs drive the progression of leukemia, analysis and characterization of that population specifically could allow for better prediction of the course of the disease.

SUMMARY

The invention provides methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC, the method comprising:

(a) (i) providing at least one or a plurality of CSCs;
(ii) detecting and quantifying in the at least one or a plurality of CSCs:
   (1) one or more B-cell lymphoma-2 (Bcl-2) family protein(s) or protein isoform(s); or
   (2) a transcript (mRNA, message) encoding one or more Bcl-2 family protein(s) or protein isoform(s); and
(iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);
wherein
   (1) increased levels of protein or transcript in the CSC as compared to the cell having the comparable normal (wild type) phenotype, or
   (2) more amount of a longer splice form of a Bcl-2 family protein transcript as compared to a shorter alternative splice isoform of the Bcl-2 family transcript,
indicates a susceptibility of the CSC to a self-renewal pathway inhibitory compound, or a lack of susceptibility of the CSC to a drug or a pro-differentiation compound or drug, or a poorer prognosis for the cancer related to the CSC;

(b) the method of (a), wherein the Bcl-2 family transcript comprises or consists of a myeloid cell leukemia sequence 1 (Mcl-1) transcript;

(c) the method of (a), wherein the Bcl-2 family transcript comprises or consists of a Bcl-XL (B-cell lymphoma-extra large) transcript;

(d) the method of (a), wherein the Bcl-2 family transcript comprises or consists of a pro-apoptotic Bcl-2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer Bcl-2 family transcript isoforms to shorter Bcl-2 family transcript isoforms, wherein the detected presence of more of a longer Bcl-2 family transcript isoform to a shorter Bcl-2 family transcript isoform indicates a susceptibility of the CSC to a self-renewal pathway inhibitory compound, or a lack of susceptibility of the CSC to a drug or a pro-differentiation compound or drug, or a poorer prognosis for the cancer related to the CSC; or (h) the method of any of (a) to (g), wherein the cancer stem cell (CSC) is a leukemia cancer stem cell (CSC).

The invention provides methods for identifying a target for a composition or drug that inhibits the self-renewal potential of a cancer stem cell (CSC), the method comprising:

(a) (i) providing at least one or a plurality of CSCs;

(ii) providing an inhibitory antisense nucleic acid or an inhibitory RNA that inhibits the expression and/or activity of one, several or all isoforms of;
  (1) one or more B-cell lymphoma-2 (Bcl-2) family protein(s) or protein isoform(s) in a CSC; or
  (2) a transcript (mRNA, message) encoding one or more Bcl-2 family protein(s) or protein isoform(s); and (iii) contacting the inhibitory antisense nucleic acid or the inhibitory RNA with the at least one or a plurality of CSCs;

(iv) measuring the self-renewal potential of the at least one or a plurality of CSCs, wherein a lowered self-renewal potential of the at least one or a plurality of CSCs after the contacting (as compared to a control cell or cells not contacted by the inhibitory antisense nucleic acid or the inhibitory RNA) identifies the inhibited protein or transcript (mRNA, message) or isoform thereof as a target for a drug or compound that will lower the self-renewal potential of the CSC;

(b) the method of (a), wherein the Bcl-2 family transcript comprises or consists of a myeloid cell leukemia sequence 1 (Mcl-1) transcript;

(c) the method of (a), wherein the Bcl-2 family transcript comprises or consists of a Bcl-XL (B-cell lymphoma-extra large) transcript;

(d) the method of (a), wherein the Bcl-2 family transcript comprises or consists of a pro-apoptotic Bcl-2 family member transcript; or (e) the method of (a) any or (a) to (d), wherein the inhibitory RNA comprises an siRNA or a ribozyme.

The invention provides methods for determining the prognosis or malignant potential of a cancer comprising:

(a) (i) providing at least one or a plurality of CSCs;

(ii) detecting and quantifying in the at least one or a plurality of CSCs:
  (1) one or more B-cell lymphoma-2 (Bcl-2) family protein(s) or protein isoform(s); or
  (2) a transcript (mRNA, message) encoding one or more Bcl-2 family protein(s) or protein isoform(s); and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein
  (1) increased levels of protein or transcript in the CSC as compared to the cell having the comparable normal (wild type) phenotype, or
  (2) more amount of a longer splice form of the Bcl-2 family transcript as compared to a shorter alternative splice isoform of the Bcl-2 family transcript, respectively, indicates a poorer prognosis for the cancer or a higher malignant potential of the cancer corresponding to the CSC;

(b) the method of (a), wherein the Bcl-2 family transcript comprises or consists of a myeloid cell leukemia sequence 1 (Mcl-1) transcript;

(c) the method of (a), wherein the Bcl-2 family transcript comprises or consists of a Bcl-XL (B-cell lymphoma-extra large) transcript;

(d) the method of (a), wherein the Bcl-2 family transcript comprises or consists of a pro-apoptotic Bcl-2 family member transcript;

(e) the method of any of (a) to (d), wherein the detecting and quantifying the transcript comprises use of a PCR protocol;

(e) the method of (d), wherein the PCR comprises a Q-RT-PCR or equivalent;

(f) the method of any of (a) to (e), wherein the method comprises determining the ratio of longer Bcl-2 family transcript isoforms to shorter Bcl-2 family transcript isoforms, wherein the detected presence of more of a longer Bcl-2 family transcript isoform to a shorter Bcl-2 family transcript isoform indicates a poorer prognosis for the cancer or a higher malignant potential of the cancer corresponding to the CSC.

The invention provides methods for determining the anti-apoptotic versus a pro-apoptotic potential of a cancer stem cell (CSC), the method comprising:

(a) (i) providing at least one or a plurality of CSCs;

(ii) detecting and quantifying in the at least one or a plurality of CSCs:
  (1) one or more B-cell lymphoma-2 (Bcl-2) family protein(s) or protein isoform(s); or
  (2) a transcript (mRNA, message) encoding one or more Bcl-2 family protein(s) or protein isoform(s); and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein
  (1) increased levels of protein or transcript in the CSC as compared to the cell having the comparable normal (wild type) phenotype, or
  (2) more amount of a longer splice form of a Bcl-2 family protein transcript as compared to a shorter alternative splice isoform of the Bcl-2 family transcript, indicates an anti-apoptotic potential of the CSC;

(b) the method of (a), wherein the Bcl-2 family transcript comprises or consists of a myeloid cell leukemia sequence 1 (Mcl-1) transcript;

(c) the method of (a), wherein the Bcl-2 family transcript comprises or consists of a Bcl-XL (B-cell lymphoma-extra large) transcript;

(d) the method of (a), wherein the Bcl-2 family transcript comprises or consists of a pro-apoptotic Bcl-2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer Bcl-2 family transcript isoforms to shorter Bcl-2 family transcript isoforms, wherein the detected presence of more of a longer Bcl-2 family transcript isoform to a shorter Bcl-2 family transcript isoform indicates an anti-apoptotic potential of the CSC; or (h) the method of any of (a) to (g), wherein the cancer stem cell (CSC) is a leukemia cancer stem cell (CSC).

The invention provides compositions and methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC, the method comprising:

(a) (i) providing at least one or a plurality of CSCs;

(ii) detecting and quantifying in the at least one or a plurality of CSCs:

(1) an activated beta-catenin protein, a protein encoded by a GSK3beta mRNA splice isoform or a Sonic Hedgehog Homolog (SHH or Shh) protein mediator; or (2) a transcript (mRNA, message) of an activated beta-catenin protein, a glycogen synthase kinase-3 beta (GSK-3 beta) transcript splice isoform, a glycogen synthase kinase-3 alpha (GSK-3 alpha) transcript splice isoform or a Shh mediator transcript; and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein (1) increased levels of protein or transcript in the CSC as compared to the cell having the comparable normal (wild type) phenotype, or (2) more amount of a longer splice isoform of GSK3beta and/or GSK3alpha transcript as compared to a shorter alternative splice isoform of GSK3beta and/or GSK3alpha transcript, respectively, indicates a susceptibility of the CSC to a self-renewal pathway inhibitory compound, or a lack susceptibility of the CSC to an anti-cancer drug or a pro-differentiation compound or drug, or a poorer prognosis for a cancer related to the CSC;

(b) the method of (a), wherein the GSK3beta splice isoform comprises or consists of an SUFU or a Gli 1;

(c) the method of (a), wherein the Shh mediator comprises or consists of a mediator of Shh, Smo, Gli or SUFU;

(d) the method of (a), wherein the detecting and quantifying the transcript comprises use of PCR;

(e) the method of (d), wherein the PCR comprises a Q-RT-PCR or equivalent;

(f) the method of any of (a) to (e), wherein the method comprises quantifying: (1) an activated beta-catenin protein, a protein encoded by a GSK3beta mRNA splice isoform and a Shh protein mediator; (2) quantifying a transcript (mRNA, message) of an activated beta-catenin protein, a GSK3beta splice isoform and a sShh mediator; or (3) both (1) and (2).

The invention provides methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC, the method comprising:

(a) (i) providing at least one or a plurality of CSCs;

(ii) detecting and quantifying in the at least one or a plurality of CSCs:

(1) a protein encoded by a Wnt and Shh mRNA splice isoform, or a Wnt or a Sonic Hedgehog Homolog (SHH or Shh) protein family member; or (2) a Wnt and Shh family member mRNA splice isoform, or a Wnt or a Shh protein-encoding mRNA; and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein (1) increased levels of protein or transcript in the CSC as compared to the cell having the comparable normal (wild type) phenotype, or (2) more amount of a longer splice isoform of a transcript as compared to a shorter alternative splice isoform of the transcript, respectively, indicates a susceptibility of the CSC to a self-renewal pathway inhibitory compound, or a lack of susceptibility of the CSC to drug or a pro-differentiation compound or drug, or a poorer prognosis for a cancer related to the CSC (b) the method of (a), wherein the Wnt family member comprises or consists of WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11 and/or WNT16;

(c) the method of (a), wherein the Shh protein comprises a preproprotein isoform or an autoprocessed form;

(d) the method of (a), wherein the detecting and quantifying the transcript comprises use of PCR;

(e) the method of (d), wherein the PCR comprises a Q-RT-PCR or equivalent; and (f) the method of any of (a) to (e), wherein the method comprises quantifying: (1) a protein encoded by a Wnt and Shh mRNA splice isoform, and a Wnt or a Shh protein family member; (2) a Wnt and Shh family member mRNA splice isoform, and a Wnt or a Shh protein-encoding mRNA; or (3) both (i) and (ii).

The invention provides methods for identifying a target for a composition or drug that inhibits the self-renewal potential of a cancer stem cell (CSC), the method comprising:

(a) (i) providing at least one or a plurality of CSCs;

(ii) providing an inhibitory antisense nucleic acid or an inhibitory RNA that inhibits the expression and/or activity of one, several or all isoforms of;

(1) an activated beta-catenin protein, a protein encoded by a GSK3beta and/or GSK3alpha mRNA splice isoform, or a Sonic Hedgehog Homolog (SHH or Shh) protein mediator; or (2) a transcript (mRNA, message) of an activated beta-catenin protein, a GSK3beta and/or GSK3alpha splice isoform or a Shh mediator; and (iii) contacting the inhibitory antisense nucleic acid or the inhibitory RNA with the at least one or a plurality of CSCs;

(iv) measuring the self-renewal potential of the at least one or a plurality of CSCs, wherein a lowered self-renewal potential of the at least one or a plurality of CSCs after the contacting (as compared to a control cell or cells not contacted by the inhibitory antisense nucleic acid or the inhibitory RNA) identifies the inhibited protein or transcript (mRNA, message) or isoform thereof as a target for a drug or compound that will lower the self-renewal potential of the CSC;

(b) the method of (a), wherein the GSK3beta splice isoform comprises or consists of an SUFU or a Gli 1;

(c) the method of (a), wherein the Shh mediator comprises or consists of a mediator of Shh, Smo, Gli or SUFU;

(d) the method of (a), wherein the inhibitory RNA comprises an siRNA or a ribozyme.

The invention provides methods for determining the prognosis or malignant potential of a cancer comprising:

(a) (i) providing at least one or a plurality of CSCs;

(ii) detecting and quantifying in the at least one or a plurality of CSCs:

(1) an activated beta-catenin protein, a protein encoded by a GSK3beta and/or GSK3alpha mRNA splice isoform or a Sonic Hedgehog Homolog (SHH or Shh) protein mediator; or (2) a transcript (mRNA, message) of an activated beta-catenin protein, a GSK3beta and/or GSK3alpha splice isoform or a Shh mediator; and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein (1) increased levels of protein or transcript in the CSC as compared to the cell having the comparable normal (wild type) phenotype, or (2) more amount of a longer splice isoform of GSK3beta and/or GSK3alpha transcript as compared to a shorter alternative splice isoform of GSK3beta and/or GSK3alpha transcript, respectively, indicates a poorer prognosis for the cancer or a higher malignant potential of the cancer corresponding to the CSC;

(b) the method of (a), wherein the GSK3beta splice isoform comprises or consists of an SUFU or a Gli 1;

(c) the method of (a), wherein the Shh mediator comprises or consists of a mediator of Shh, Smo, Gli or SUFU;

(d) the method of (a), wherein the detecting and quantifying the transcript comprises use of a PCR protocol;

(e) the method of (d), wherein the PCR comprises a Q-RT-PCR or equivalent;

(f) the method of any of (a) to (e), wherein the method comprises quantifying: (1) an activated beta-catenin protein, a protein encoded by a GSK3beta mRNA splice isoform and a Shh protein mediator; (2) quantifying a transcript (mRNA, message) of an activated beta-catenin protein, a GSK3beta splice isoform and a sShh mediator; or (3) both (1) and (2).

The invention provides methods for determining the prognosis or malignant potential of a cancer comprising:

(a) (i) providing at least one or a plurality of CSCs;

(ii) detecting and quantifying in the at least one or a plurality of CSCs:

(1) a protein encoded by a Wnt and Shh mRNA splice isoform, or a Wnt or a Sonic Hedgehog Homolog (SHH or Shh) protein family member; or (2) a Wnt and Shh family member mRNA splice isoform, or a Wnt or a Shh protein-encoding mRNA; and (iii) comparing (1) the quantified levels of protein or transcript in the CSC to a cell having a comparable normal (wild type) phenotype, or (2) the amount of one protein isoform to a second protein isoform (of the same protein), or the amount of transcript encoding one protein isoform to the amount of transcript encoding a second protein isoform (of the same protein);

wherein (1) increased levels of protein or transcript in the CSC as compared to the cell having the comparable normal (wild type) phenotype, or (2) more amount of a longer splice isoform of a transcript as compared to a shorter alternative splice isoform of the transcript, respectively, indicates a poorer prognosis or a malignant potential for a cancer corresponding to the CSC;

(b) the method of (a), wherein the Wnt family member comprises or consists of WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11 and/or WNT16;

(c) the method of (a), wherein the Shh protein comprises a preproprotein isoform or an autoprocessed form;

(d) the method of (a), wherein the detecting and quantifying the transcript comprises use of a PCR protocol;

(e) the method of (d), wherein the PCR comprises a Q-RT-PCR or equivalent; and (f) the method of any of (a) to (e), wherein the method comprises quantifying: (1) a protein encoded by a Wnt and Shh mRNA splice isoform, and a Wnt or a Shh protein family member; (2) a Wnt and Shh family member mRNA splice isoform, and a Wnt or a Shh protein-encoding mRNA; or (3) both (i) and (ii).

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

FIG. 1 illustrates results from chronic myeloid leukemia (CML) Blast Crisis Progenitor CD34+CD38+Lin− Transplant Leukemia studies: FIG. 1—Middle: illustrates hematoxylin-eosin stained tumor tissue; FIG. 1 Right—illustrates a nested primer RT-PCR for P210 BCR-ABL; as described in detail in Example 1, below.

FIG. 2 D illustrates an averaged normalized Bcl-2 FITC MFI of the progenitor (CD34$^+$CD38$^+$Lin$^-$) population of CML CP and CML BC samples; as described in detail in Example 1, below.

FIG. 3 illustrates results from studies showing CML BC-Derived Tumors Differentially Express Mcl-1 Splice Isoforms.

FIG. 4 illustrates results from studies showing that apogossypol Treatment inhibits CML BC Progenitor Engraftment.

In FIG. 9: the sense strand of the 001__1AB_B fragment is SEQ ID NO:1, and the antisense strand is SEQ ID NO:2; the sense strand of the 006__1AF_J fragment is SEQ ID NO:3, and the antisense strand is SEQ ID NO:4; the sense strand of the 001__1AJ_J fragment is SEQ ID NO:5, and the antisense strand is SEQ ID NO:6; the sense strand of the A02__1AB_J fragment is SEQ ID NO:7, and the antisense strand is SEQ ID NO:8; the sense strand of the E06__2AF_J fragment is SEQ ID NO:9, and the antisense strand is SEQ ID NO:10; the sense strand of the G02__2AJ_J fragment is SEQ ID NO:11, and the antisense strand is SEQ ID NO:12; the sense strand of the E03__2AB_J fragment is SEQ ID NO:13, and the antisense strand is SEQ ID NO:14; the sense strand of the G03__3AJ_J fragment is SEQ ID NO:15, and the antisense strand is SEQ ID NO:16; the sense strand of the CD4__3AB_I fragment is SEQ ID NO:17, and the antisense strand is SEQ ID NO:18; and, the sense strand of the C03__3AB_J fragment is SEQ ID NO:19, and the antisense strand is SEQ ID NO:20.

DETAILED DESCRIPTION

Figure 1A:
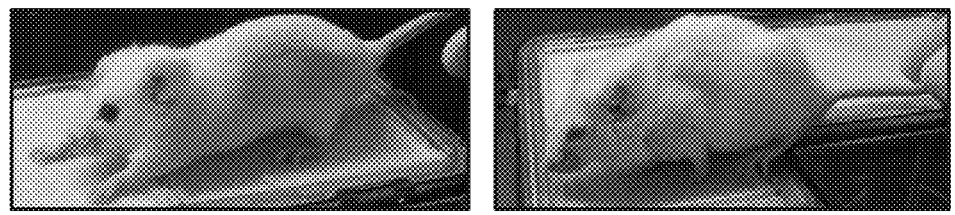
FIG. 1A illustrates neonatal RAG2−/−$\gamma_c$−/− mice transplanted intra-hepatically with BC CML progenitors.

The invention provides compositions and methods to determine the self-renewal potential of cancer stem cells (CSCs) through analysis of the cross-talk between self-renewal pathways leading to deregulation and enhanced self-renewal of the CSCs.

While the invention is not limited by any particular mechanism of action, this invention characterizes how CML CSC deregulate apoptosis pathways by differential expression of Bcl-2 family molecules, and that these changes contribute to CSC ability to survive serial transplantation; this invention describes the relationship between isoforms of Bcl-2 family members and the balance of pro-apoptotic and anti-apoptotic signals in cancer and CSC cells.

In one embodiment, the methods comprise quantification of at least one, several or all of the following: one or more B-cell lymphoma-2 (Bcl-2) family protein(s) or protein isoform(s); or (2) a transcript (mRNA, message) encoding one or more Bcl-2 family protein(s) or protein isoform(s).

In one embodiment, an alternatively or aberrantly spliced Bcl-2 transcript is detected and measure, e.g., the amount of longer versus shorter Bcl-2 transcripts are detected and quantified. For example, in one embodiment, the presence of longer versus shorter Bcl-2 splice isoforms is predictive of enhanced self-renewal potential of a CSC. Bcl-2 messages (transcripts), including alternatively or aberrantly spliced Bcl-2 message (transcript) isoforms, can be detected and/or quantified by PCR, e.g., by splice isoform specific Q-RT-PCR. In one embodiment, the methods comprise quantification of any one, several or all of these markers Bcl-2 splice isoform(s).

In one embodiment, the compositions and methods of the invention are used as a method of predicting increased self-renewal of a CSC, and its capacity to be inhibited by targeted self-renewal pathway inhibitors. In alternative embodiments, these exemplary methods allow for determination of a CSC cell's self-renewal state and allow for prediction of the drugability (e.g., susceptibility to a drug) of a CSC, and the progression of the corresponding cancer. For example, in one embodiment, detection and quantifying that the cell contains more of the longer splice isoform of a Bcl-2 message (transcript) than a shorter splice isoform of the Bcl-2 message (transcript) is predictive of an increased CSC cell self-renewal state, i.e., predictive of an enhanced self-renewal potential of a CSC.

While the invention is not limited by any particular mechanism of action, compositions and methods of the invention can predict increased self-renewal of a CSC and its capacity to be inhibited by targeted self-renewal pathway inhibitors because the levels of the longer splice isoform of a Bcl-2 message (transcript, mRNA) in a cell often determines whether that cell is susceptible to self-renewal pathway inhibitory drugs; thus, the characterization of Bcl-2 message (transcript, mRNA) expression allows for prediction of the drug-susceptibility of CSCs.

With respect to the quantification of Bcl-2 family mRNAs, compositions and methods of the invention can detect and/or differentiate between all of the isoforms of a particular gene or message, e.g., all of the isoforms of a Bcl-2 family gene and/or mRNA isoform. By detecting and differentiating between all of the isoforms of a particular gene or message, rather than the total amount of only one splice isoform, e.g., a longer Bcl-2 splice isoform or a shorter Bcl-2 family member splice isoform (which would not necessarily correspond to the self-renewal state of the cell), the invention by measuring both longer and shorter isoforms (or all of several possible alternatively spliced isoforms that are present at one time in a cell) can better determine whether there are changes in the balance of pro-self-renewal (anti-differentiation) and pro-differentiation signals.

In one embodiment, the compositions and methods of the invention are used to detect and/or differentiate all of several possible alternatively spliced Bcl-2 isoform family molecules; e.g., for Mcl-1a longer gene product (isoform 1) can enhance cell survival by inhibiting apoptosis while the alternatively spliced shorter gene product (isoform 2) can promote apoptosis and is death-inducing. This invention for the first time describes the molecular cross-talk between alternatively spliced Bcl-2 isoform family molecules and other proteins involved in cell cycle and/or apoptosis.

In one embodiment, compositions and methods of the invention provide for RNA silencing (e.g., shRNA silencing) of Bcl-2 family transcripts in CSCs to predict the potency of Bcl-2 family molecules in CSC self-renewal and for predicting the clinical potential of targeted Bcl-2 inhibition or Bcl-2 enhancement with e.g. a drug or a small molecule.

In alternative embodiments, compositions and methods of the invention can use any flow cytometry method, any PCR and/or any immunohistochemistry technique to characterize the molecular expression of leukemia cells or a CSC population. In alternative embodiments, compositions and methods of the invention focus on detecting and quantifying Bcl-2 family expression changes in a CSC population.

In one embodiment, compositions and methods of the invention quantify protein, e.g., a Bcl-2 family protein, in CSC by flow cytometry, e.g., FACS, e.g., a rapid FACS-based analysis. In one embodiment, peripheral blood mononuclear cells (PBMCs) are harvested from leukemic blood or bone marrow samples. The PBMCs are run through a CD34 selection column and are then surface stained with fluorescence-conjugated antibodies. The cells are fixed with paraformaldehyde, permeabilized with saponin, and finally stained intracellularly with fluorescence-conjugated antibodies to detect Bcl-2 family proteins. The stained cells are run on a FACS Aria cell sorter and the CD34+CD38+lineage– staining fraction is analyzed for Bcl-2 family protein expression.

In one embodiment, compositions and methods of the invention quantify message (mRNA) using PCR, e.g., using qPCR, using splice isoform-specific primers to quantitate the amount of splice isoforms of Bcl-2 family proteins. In one embodiment, the quantitation is then used to determine the splice isoform ratio which gives a relative determination of whether cells are more pro-apoptotic or more anti-apoptotic. In alternative embodiments, mRNA quantification using qPCR and splice isoform-specific primers to quantitate the amount of splice isoforms of Bcl-2 family proteins allows quantitation and determination of the long Bcl-2 (e.g., Mcl-1) transcript versus short Bcl-2 (e.g., Mcl-1) transcript splice isoform ratio which gives a relative determination of whether cells are more pro-apoptotic or more anti-apoptotic.

In one embodiment, compositions and methods of the invention use nucleic acids, e.g., inhibitory or antisense RNA, e.g., shRNA, to "knockdown" (e.g., turn down or turn off) Bcl-2 (e.g., Mcl-1) family transcript expression as a means of determining the predominant pathways required for CSC self-renewal. In one embodiment, the inhibitory or antisense RNA, e.g., shRNA, are incorporated into a vector, e.g., a lentiviral vector, and are introduced into CSCs, e.g., by transfection or transduction. The effects of transcript knockdown on CSC self-renewal can be assayed, e.g., using a RAG–/– $y_c$–/– xenograft model, and/or using in vitro in methylcellulose assays, and the like.

The compositions and methods of this invention also can be used to determine and measure the level of Bcl-2 (e.g., Mcl-1) family proteins and transcript ratios in CSCs for prognostic reasons, e.g., to predict cancer progression and/or to predict whether the CSCs will be susceptible to certain therapeutic drugs. Thus, the compositions and methods of this invention also can be applicable to CSCs in a number of malignancies including CML.

Polypeptides and Peptides

In alternative embodiments, the invention provides compositions and methods to determine and measure the levels of Bcl-2 (e.g., Mcl-1) family proteins and transcripts, and/or Bcl-2 (e.g., Mcl-1) family protein and transcript ratios in stem cells, e.g., CSCs, for diagnostic, drug discovery and prognostic reasons.

Polypeptides and peptides used to practice the invention (e.g., as controls, to raise antibodies to Bcl-2 (e.g., Mcl-1) family proteins) can comprise a recombinant protein, a synthetic protein, a peptidomimetic, a non-natural peptide, or a combination thereof. Peptides and proteins used to practice the invention can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) including any automated polypeptide synthesis process known in the art.

Antibodies

In alternative embodiments, compositions and methods of the invention comprise use of antibodies to determine and measure the levels of Bcl-2 (e.g., Mcl-1) family proteins and transcripts, and/or Bcl-2 (e.g., Mcl-1) family protein and transcript ratios in stem cells, e.g., CSCs, for diagnostic, drug discovery and prognostic reasons.

In alternative aspects, an antibody for practicing the invention can comprise a peptide or polypeptide derived from, modeled after or substantially encoded by a Bcl-2 family protein, or immunogenic fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing the invention includes antigen-binding portions, i.e., "antigen binding sites," (e.g., fragments, subsequences, complementarity determining regions (CDRs)) that retain capacity to bind antigen (e.g., a Bcl-2 family protein, or immunogenic fragments thereof) including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii)

a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu Rev. Biophys. Biomol. Struct. 26:27-45.

In alternative embodiments, antibodies used to practice this invention comprise "affinity matured" antibodies, e.g., antibodies comprising with one or more alterations in one or more hypervariable regions which result in an improvement in the affinity of the antibody for antigen; e.g., a Bcl-2 (e.g., Mcl-1) family protein, or immunogenic fragments thereof. In alternative embodiments, antibodies used to practice this invention are matured antibodies having nanomolar or even picomolar affinities for the target antigen, e.g., a targeted transcriptional activating factor. Affinity matured antibodies can be produced by procedures known in the art.

Generating and Manipulating Nucleic Acids

In alternative embodiments, the method of the invention use nucleic acids for detecting and quantifying levels of a transcript (mRNA, message) of a Bcl-2 (e.g., Mcl-1) transcript splice isoform. In alternative embodiments, the method of the invention use nucleic acids for detecting and quantifying levels of a transcript (mRNA, message) of a longer mRNA splice isoform versus a shorter Bcl-2 (e.g., Mcl-1) isoform.

In alternative embodiments, nucleic acids of the invention are made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including e.g. bacterial, fungal, mammalian, yeast, insect or plant cell expression systems.

Alternatively, nucleic acids used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Nucleic acids or nucleic acid sequences used to practice this invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice this invention include genes or any segment of DNA or RNA involved in producing a polypeptide chain; it can include regions preceding and following the coding region (leader and trailer) as well as, where applicable, intervening sequences (introns) between individual coding segments (exons). "Operably linked" can refer to a functional relationship between two or more nucleic acid (e.g., DNA or RNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequence used to practice this invention, which can be capable of affecting expression of the nucleic acid, e.g., a structural gene or a transcript (e.g., encoding a DRP or antibody) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector" used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

"Constitutive" promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions.

Antisense Inhibitory Nucleic Acid Molecules

In alternative embodiments, the invention provides methods for identifying a target for a composition or drug that inhibits the self-renewal potential of a cancer stem cell (CSC), the method comprising: (a) (i) providing at least one or a plurality of CSCs; (ii) providing an inhibitory antisense nucleic acid or an inhibitory RNA that inhibits the expression and/or activity of one, several or all of the Bcl-2 (e.g., Mcl-1) isoforms in the CSC cell; and (iii) contacting the inhibitory antisense nucleic acid or the inhibitory RNA with the at least one or a plurality of CSCs; (iv) measuring the self-renewal potential of the at least one or a plurality of CSCs, wherein a lowered self-renewal potential of the at least one or a plurality of CSCs identifies the inhibited protein or transcript (mRNA, message) as a target for a drug or compound that will lowered self-renewal potential of the CSC.

Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids.

RNA Interference (RNAi)

In one aspect, the invention provides RNAi inhibitory nucleic acid molecules capable of decreasing or inhibiting expression of one or a set of transcripts or proteins, e.g., a Bcl-2 (e.g., Mcl-1) transcript (mRNA, message) or isoform or isoforms thereof. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand can be specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a gene, e.g., an NADPH oxidase enzyme coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA of the invention.

Alternatively, a targeted portion of a gene, coding sequence, promoter or transcript can be designed as a first and second antisense binding region together on a single expression vector; for example, comprising a first coding region of a targeted gene in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene-inhibitory siRNA used to practice this invention.

In another aspect, transcription of the sense and antisense targeted portion of the targeted gene is controlled by a single promoter, and the resulting transcript will be a single hairpin RNA strand that is self-complementary, i.e., forms a duplex by folding back on itself to create a gene-inhibitory siRNA molecule. In this configuration, a spacer, e.g., of nucleotides, between the sense and antisense coding regions of the targeted portion of the targeted gene can improve the ability of the single strand RNA to form a hairpin loop, wherein the hairpin loop comprises the spacer. In ones embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

The invention provides ribozymes capable of binding and inhibiting, e.g., decreasing or inhibiting, expression of one or a set of transcripts or proteins, e.g., a Bcl-2 (e.g., Mcl-1) isoform or isoforms thereof.

These ribozymes can inhibit a gene's activity by, e.g., targeting a genomic DNA or an mRNA (a message, a transcript). Strategies for designing ribozymes and selecting a gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Kits and Instructions

The invention provides kits comprising compositions and/or instructions for practicing methods of the invention. As such, kits, cells, vectors and the like can also be provided.

The invention will be further described with reference to the following examples; however, it is to be understood that the invention is not limited to such examples.

EXAMPLES

Example 1

Deregulated BCL-2-Family Expression Drives Chronic Myeloid Leukemia Cancer Stem Cell Survival This invention for the first time elucidates how Bcl-2 family proteins are involved in CML progression and the importance of these proteins in CSC survival, and provides compositions and methods for determining the self-renewal potential of a cancer stem cell (CSC) through analysis of the cross-talk between cell self-renewal pathways leading to deregulation and enhanced self-renewal of the CSC, or for predicting the drugability (susceptibility to a drug) of a CSC, and/or for predicting the progression of a cancer that corresponds to the CSC by measuring the amount of a B-cell lymphoma-2 (Bcl-2) family protein(s) or protein isoform(s) in a CSC.

The inventors for the first time demonstrate that CML CSC deregulate apoptosis pathways by differential expression of Bcl-2 family molecules and that these changes contribute to CSC ability to survive serial transplantation. While the invention in not limited by any particular mechanism of action, CML stem cells become more resistant to therapies targeting BCR-ABL with progression to blast crisis; and as BCR-ABL targeted therapy initiates apoptosis, CML CSC becomes increasingly resistant to apoptosis with progression. The compositions and methods of the invention can manipulate CML CSC deregulated apoptosis pathways by manipulating the differential expression of Bcl-2 family molecules, and these manipulated changes can contribute to decreased CSC ability to survive serial transplantation.

Methods:

Quantitative FACSARIA™ (BD Biosciences, San Jose, Calif.) analysis of Bcl-2 protein levels was compared in blast crisis (n=6) and chronic phase CML (n=4) patient samples and in blast crisis derived myeloid sarcomas (n=5). Mean fluorescence intensity (MFI) of Bcl-2 staining was compared between different hematopoietic populations within the samples.

For gene expression analysis, cDNA was made from RNA isolated from sorted progenitor populations (CD34$^+$CD38$^+$Lin$^-$). Isoform specific RT-PCR was used to determine expression levels of Bcl-2, Bcl-X, and Mcl-1 isoforms. Expression was confirmed using qPCR.

In addition, preliminary experiments were performed (n=2) to determine if CSC engraftment could be reduced in vivo by targeted inhibition of Bcl-2 family molecules using apogossypol, a clinically tested Bcl-2-family inhibitor. Briefly, immunocompromised neonatal mice were transplanted intrahepatically with luciferase GFP transduced myeloid sarcomas from mice transplanted with BC CSC, the methodology described in Geron et al, Cancer Cell 2008; 13(4):321-30. Transplanted mice were treated for 15 days with Apogossypol by oral gavage[8] and engraftment was monitored by weekly bioluminescent imaging. Engraftment levels were determined by FACS analysis of human CD45$^+$ expression in mouse livers on week 11 post-transplant.

Results:

Comparing the MFI of Bcl-2 staining in the entire live mononuclear cell population, we detected no statistically significant difference in levels between the blast crisis and chronic phase samples. However, when we gated on separate cell populations, differences in the Bcl-2 MFI emerged. There was a statistically significant increase (P=0.01) in Bcl-2 MFI exclusively in the CD34$^+$CD38$^+$lineage$^-$ population of the blast crisis samples indicative of cell type and context specific deregulation of apoptosis in the CSC population.

Further, we were interested in whether there were differences in Bcl-2 family expression at the transcriptional level. Notably, while we detected no difference in the levels of the isoforms of Bcl-2 and Bcl-X, splice isoform specific RT-PCR and qPCR revealed a decrease in the expression of the short isoform of Mcl-1, which encodes a pro-apoptotic protein, in serially transplanted BC CSC(CD34$^+$CD38). Together these results indicate that CML CSC may indeed deregulate the expression of several Bcl-2 family proteins.

To test the therapeutic potential of inhibiting these deregulated apoptotic pathways in CML, we treated mice engrafted with CML CSC with Apogossypol, a broad-spectrum inhibitor of pro-survival Bcl-2 molecules. We saw a statistically significant decrease (P=0.03) in the number of CD45$^+$ cells engrafted in the mouse liver after 3 weeks of Apogossypol treatment.

Overall, our results demonstrate that the subversion of apoptosis plays an important role in allowing CML CSC to be serially transplanted and that this invention's manipulation of apoptotic pathways is useful as a methodology for investigating and screening for therapeutics aimed at inhibiting these cells.

FIG. 1, below: CML Blast Crisis Progenitors (CD34+CD38+Lin−) Transplant Leukemia:

FIG. 1A illustrates: Neonatal RAG2−/−γ$_c$−/− mice transplanted intrahepatically with BC CML progenitors (34$^+$38$^+$Lin$^-$; 10$^5$) show signs of leukemia including wasting, piloerection, and lethargy by 6 weeks post-transplant.

Figure 1B:
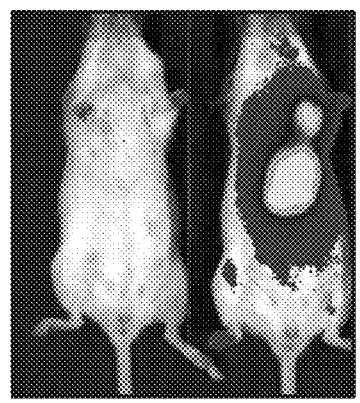
FIG. 1B illustrates transplantation of lentiviral luciferase transduced BC CML progenitors into neonatal RAG2−/−$\gamma_c$−/− mice.

FIG. 1B illustrates: Transplantation of lentiviral luciferase transduced BC CML progenitors (34$^+$38$^+$Lin$^-$; 10$^5$) into neonatal RAG2−/−γ$_c$−/− mice results in prominent tumor bioluminescence.

Figure 1C:
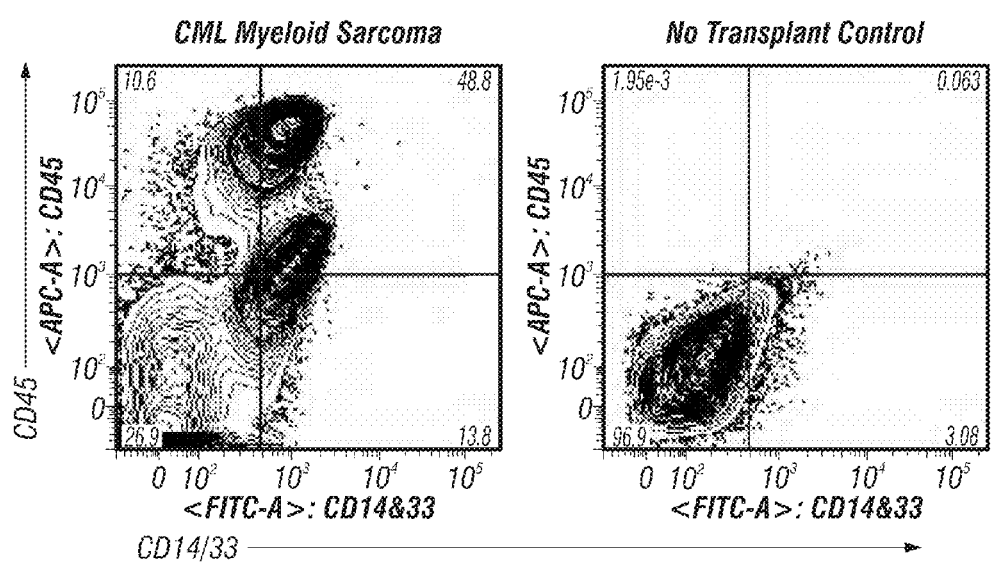
FIG. 1C illustrates a representative FACS analysis gated on the live (PI negative) fraction of a tumor single cell suspension from a mouse transplanted with CML BC progenitors.

FIG. 1C illustrates: Representative FACS analysis gated on the live (PI negative) fraction of a tumor single cell suspension from a mouse transplanted with CML BC progenitors demonstrates 87.4% human engraftment consisting of 29% human myeloid cells compared with no transplant-control marrow.

Figure 1D:
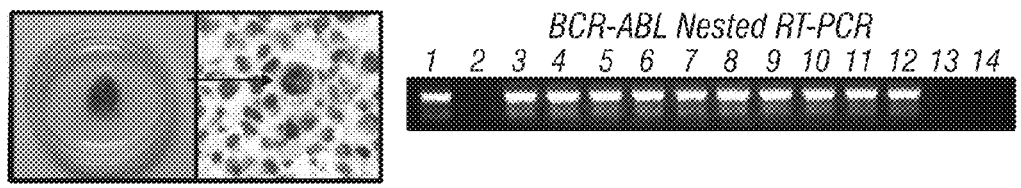
FIG. 1D illustrates—Left: illustration of a photograph of a tumor derived from a mouse transplanted with BC CML progenitors.
Figure 2A:
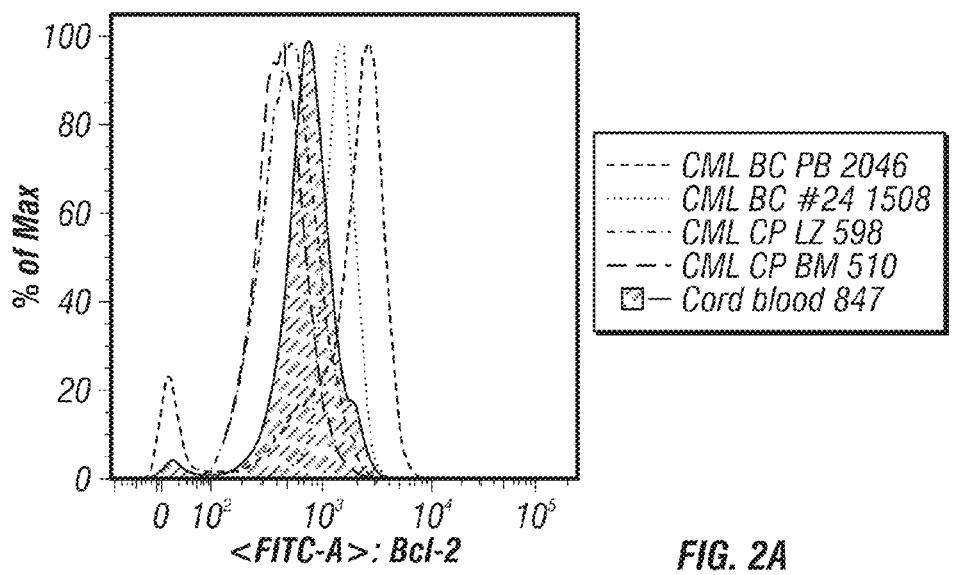
FIG. 2A illustrates a representative Bcl-2-FITC staining profile of the PI$^-$ population of CML BC (n=2), CML CP (n=2) and cord blood control samples; illustrates
Figure 2B:
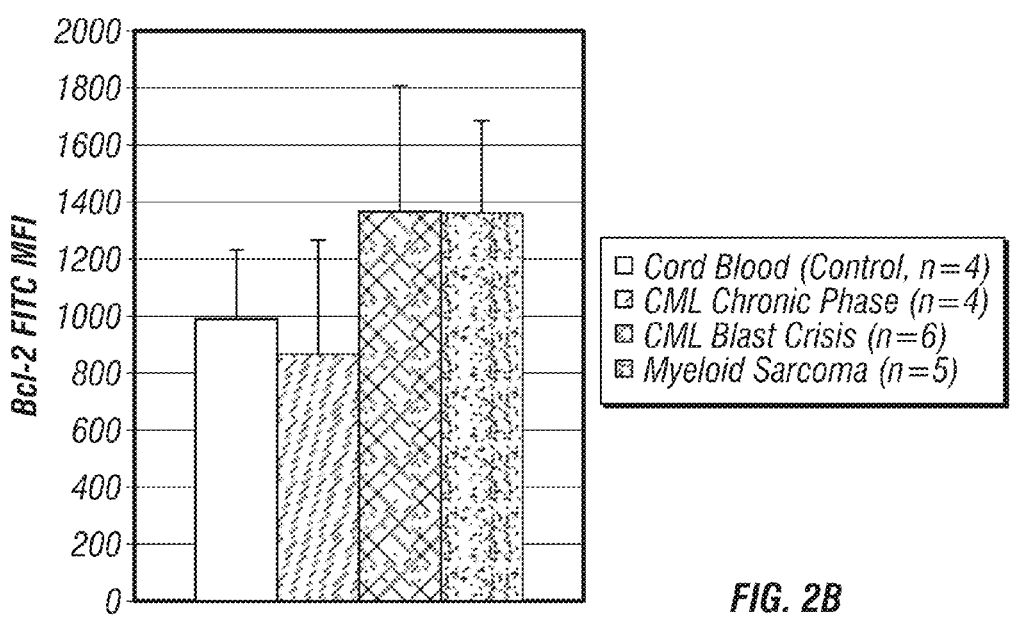
FIG. 2B illustrates average Bcl-2-FITC mean fluorescence intensity (MFI) of the PI$^-$ population of cord blood (n=4), CML CP (n=4), CML BC (n=6), and CML BC-derived tumor (n=5) samples.
Figure 2C:
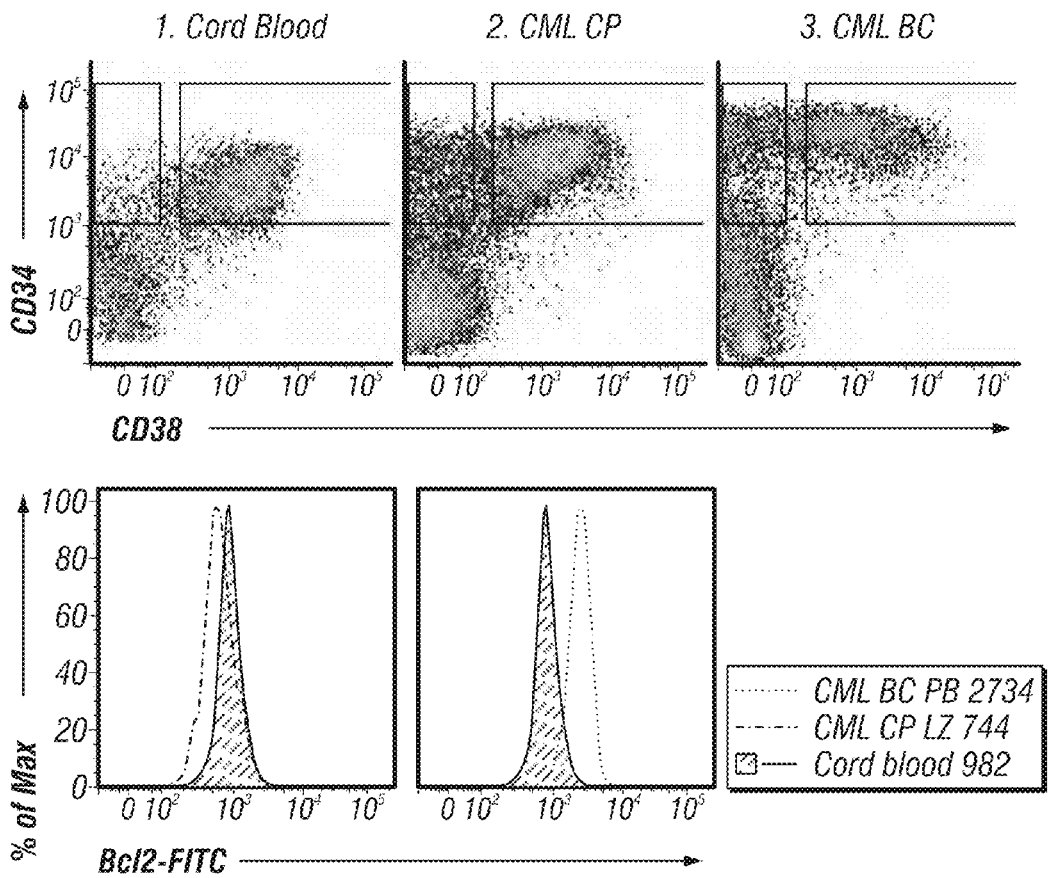
FIG. 2C illustrates—Top: illustrates a representative FACS staining profile of cord blood, CML CP, and CML BC samples, and Bottom—illustrates a Bcl-2 FITC staining of the progenitor (CD34$^+$CD38$^+$Lin$^-$) population from the above samples.
Figure 2D:
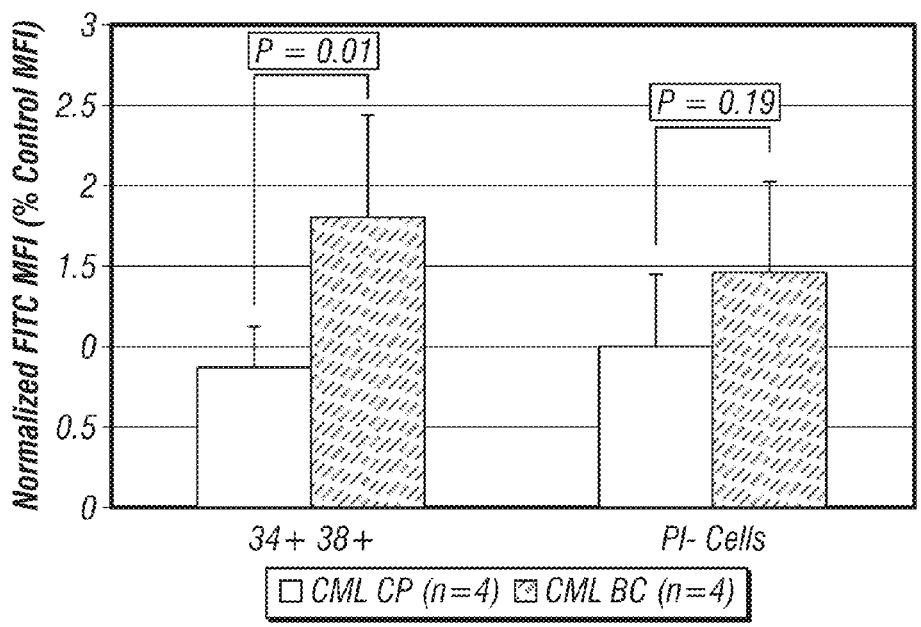
FIG. 2 illustrates results from studies showing that CML BC Progenitors Over-express Bcl-2.

FIG. 1D Left: illustration of a photograph of a tumor, in a 35 mm tissue culture dish, derived from a mouse transplanted with BC CML progenitors (34$^+$38$^+$Lin$^-$; 10$^5$). These types of tumors were detected in mice transplanted with either BC CML CD34$^+$CD38$^+$Lin$^-$ cells or BC CML CD34$^+$CD38$^+$Lin$^-$ cells.

FIG. 1 Middle: illustrates a hematoxylin-eosin stained tumor tissue revealed prominent infiltration with human myeloid cells characteristic of a BC CML granulocytic sarcoma.

FIG. 1 Right: illustrates a nested primer RT-PCR for P210 BCR-ABL. 1=P210 BCR-ABL positive control, CML patient marrow; 2=Negative control, 293T; 3=34$^+$38$^+$ Thymus; 4=34$^+$38$^+$ Spleen; 5=34$^+$38$^+$ Liver; 6=34$^+$38$^+$ Bone Marrow; 7=34$^+$38$^+$ Tumor #1; 8=34$^+$38$^+$ Tumor #2; 9=34$^+$38$^+$ Tumor #3; 10=34$^+$38$^+$ Tumor #4; 11=34$^+$38$^+$ Tumor #5; 12=34$^+$38$^+$ Tumor #6; 13=Blank; 14=Blank.

Nested BCR-ABL PCR revealed 1 positive tumor from 34$^+$38$^-$ transplanted cells and 9 positive tumors from 34$^+$38$^+$ transplanted cells.

FIG. 2, below: CML BC Progenitors Over-express Bcl-2

FIG. 2 A. Representative Bcl-2-FITC staining profile of the PI$^-$ population of CML BC (n=2), CML CP (n=2), and cord blood control samples demonstrates an overall increase in the Bcl-2 protein expression of CML BC cells compared with both CML CP cells and cord blood cells.

FIG. 2 B. Average Bcl-2-FITC mean fluorescence intensity (MFI) of the PI$^-$ population of cord blood (n=4), CML CP (n=4), CML BC (n=6), and CML BC-derived tumor (n=5) samples. BC and tumor samples show a trend toward higher overall Bcl-2 protein expression, however there is no statistically significant difference between these samples and the cord blood and CML CP samples (p=0.11).

FIG. 2 C. Top: Representative FACS staining profile of cord blood, CML CP, and CML BC samples demonstrating the progenitor (CD34$^+$CD38$^+$Lin$^-$) population. Bottom: Bcl-2 FITC staining of the progenitor (CD34$^+$CD38$^+$Lin$^-$) population from the above samples shows an increase in Bcl-2 protein expression between the CML BC and CML CP and cord blood samples.

FIG. 2 D. Average normalized Bcl-2 FITC MFI (sample MFI/control MFI) of the progenitor (CD34$^+$CD38$^+$Lin$^-$) population of CML CP (n=4) and CML BC (n=6) samples shows a statistically significant difference of Bcl-2 expression between CP and BC samples (p=0.01). In comparison there is no statistically significant difference detected if the samples are gated only on the PI$^-$ population (p=0.19).

Figure 3A:
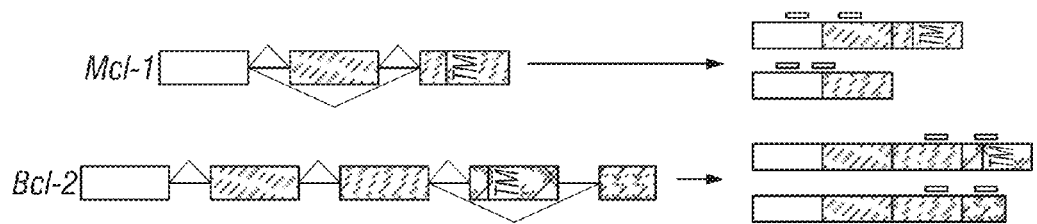
FIG. 3A illustrates that many Bcl-2 family mRNAs have 2 or more splice isoforms that produce proteins with varying function, where the splice isoforms for Mcl-1 (top) and Bcl-2 (bottom) are shown.

FIG. 3, below: CML BC-Derived Tumors Differentially Express Mcl-1 Splice Isoforms FIG. 3 A. Many Bcl-2 family mRNAs have 2 or more splice isoforms that produce proteins with varying function. The splice isoforms for Mcl-1 (top) and Bcl-2 (bottom) are shown. The red lines indicate primer sites for isoform-specific qPCR (C).

Mcl-1: The main transcript of Mcl-1 encodes a protein with a 3' transmembrane (TM) domain and with a pro-survival function. The alternate transcript for Mcl-1 is lacking exon 2. This leads to a frameshift and loss of the TM domain. This transcript encodes a protein with a pro-death function.

Bcl-2: The main transcript of Bcl-2 includes a 3' exon with a TM domain and encodes a pro-survival protein. Alternative splicing of the 3' exon leads to an alternate transcript with no TM domain. It is not clear whether the encoded protein is pro-death or pro-survival.

Figure 3B:
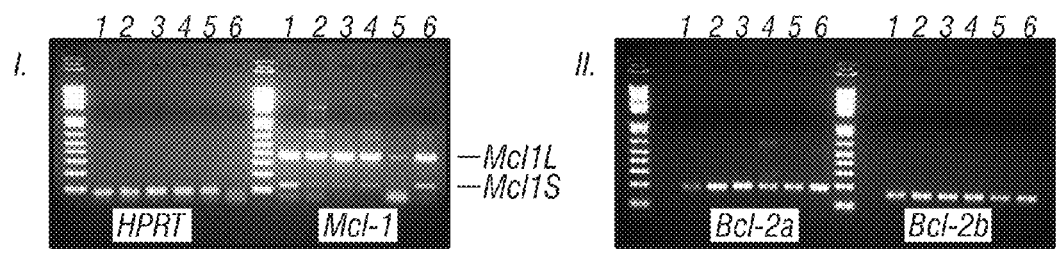
FIG. 3B illustrates an RT-PCR of HPRT (I, left), Mcl-1 (I, right), Bcl-2α (II, left), and Bcl-2β (II, right)
Figure 3C:
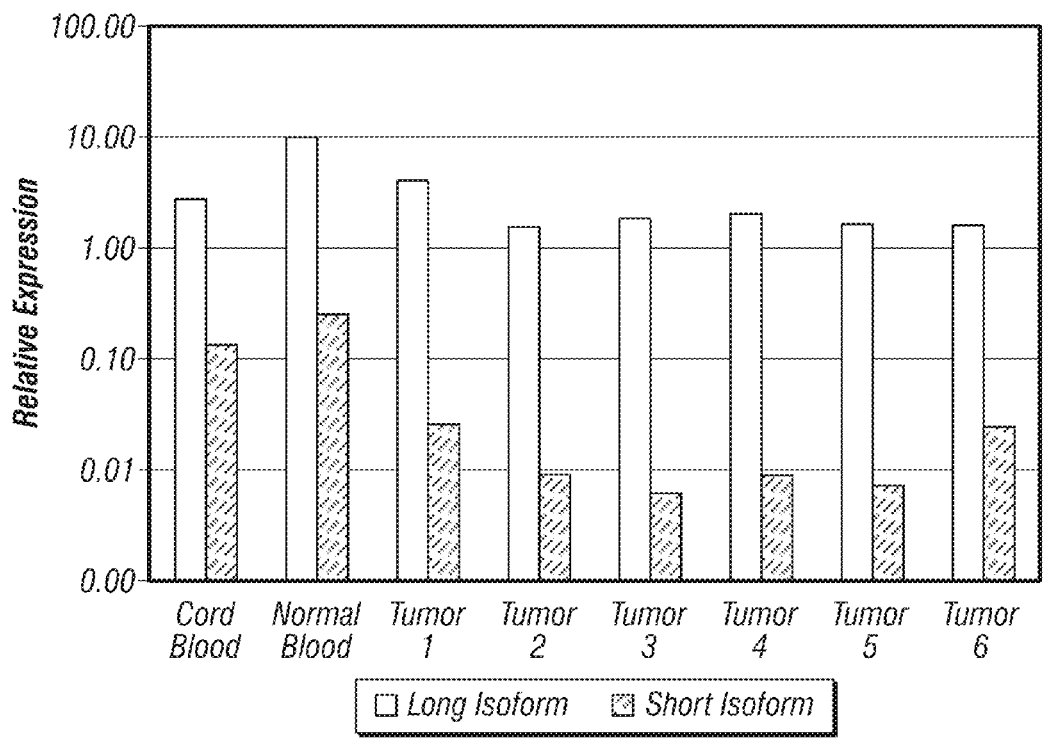
FIG. 3C illustrates—Left: illustrates a qPCR analysis of Mcl-1 long (blue) and short (red) transcripts from progenitors (CD34$^+$CD38$^+$Lin$^-$) of several normal and CML samples, and Right illustrates the Ratio of Mcl-1 long and short isoforms in the above samples; as described in detail in Example 1, below.

FIG. 3B. RT-PCR of HPRT (I, left), Mcl-1 (I, right), Bcl-2α (II, left), and Bcl-2β (II, right) showing that peripheral blood mononuclear cells (PBMC's) from CML and normal patient samples express both splice isoforms of Mcl-1 and Bcl-2. 1=Normal cord blood; 2=CML CP; 3=CML Tumor 1; 4=CML BC 1; 5=CML BC 2; 6=Normal peripheral blood FIG. 3C. Left: qPCR analysis of Mcl-1 long (blue) and short (red) transcripts from progenitors (CD34$^+$CD38$^+$Lin$^-$) of several normal and CML samples. CML BC-derived tumor cells tend to express normal levels of the Mcl-1 long isoform but less of the Mcl-1 short isoform. All values are normalized to HPRT expression (not shown).

Right: Ratio of Mcl-1 long and short isoforms in the above samples demonstrates skewed expression of Mcl-1 mRNA in CML BC-derived tumor progenitors.

FIG. 4 below. Apogossypol Treatment inhibits CML BC Progenitor Engraftment. FIG. 4A. Structure of gossypol and its derivative apogossypol. Both compounds inhibit 5 of 6 pro-survival Bcl-2 family proteins (Bcl-xL, Bcl-2, Bcl-w, Mcl-1, and Bcl-b) at $IC_{50}$<10 µM.

Figure 4A:
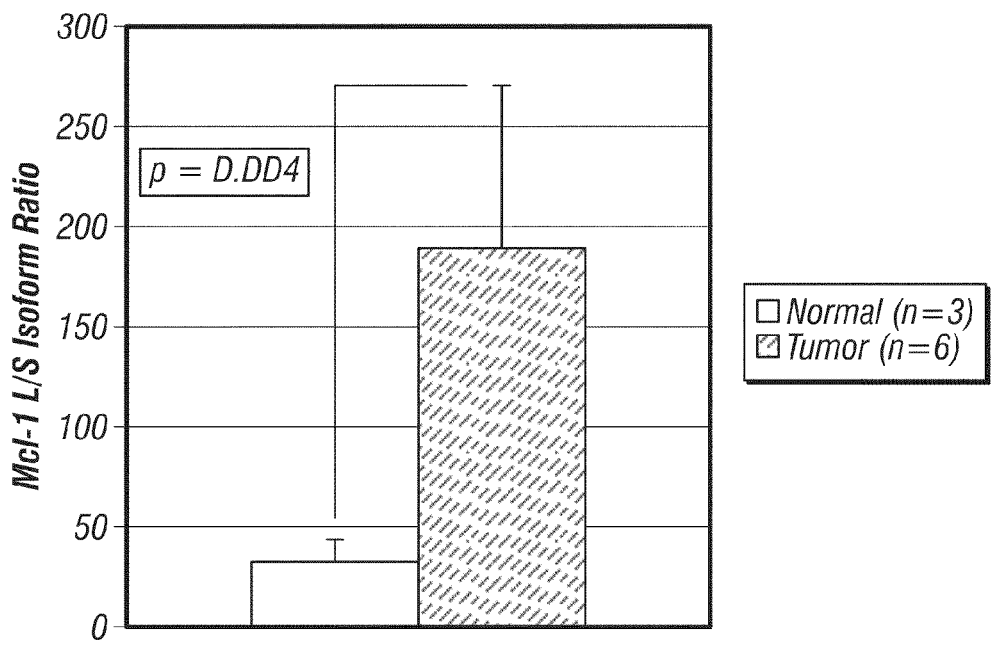
FIG. 4A illustrates the structure of gossypol and its derivative apogossypol.
Figure 4A:
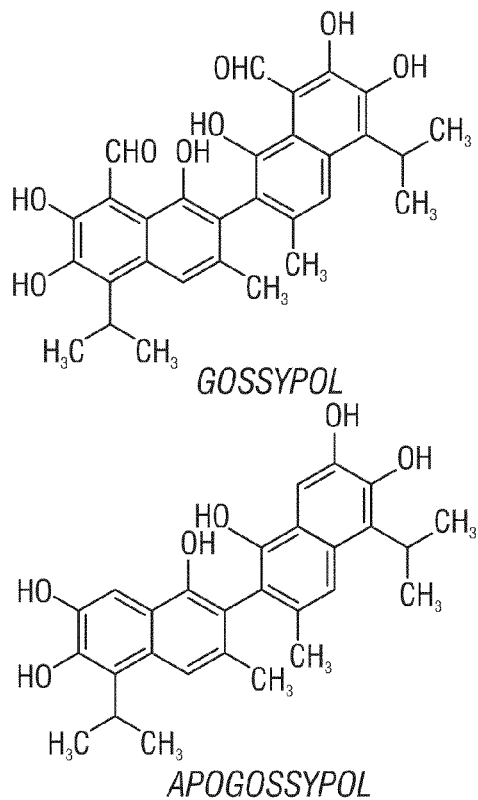
Figure 4B:
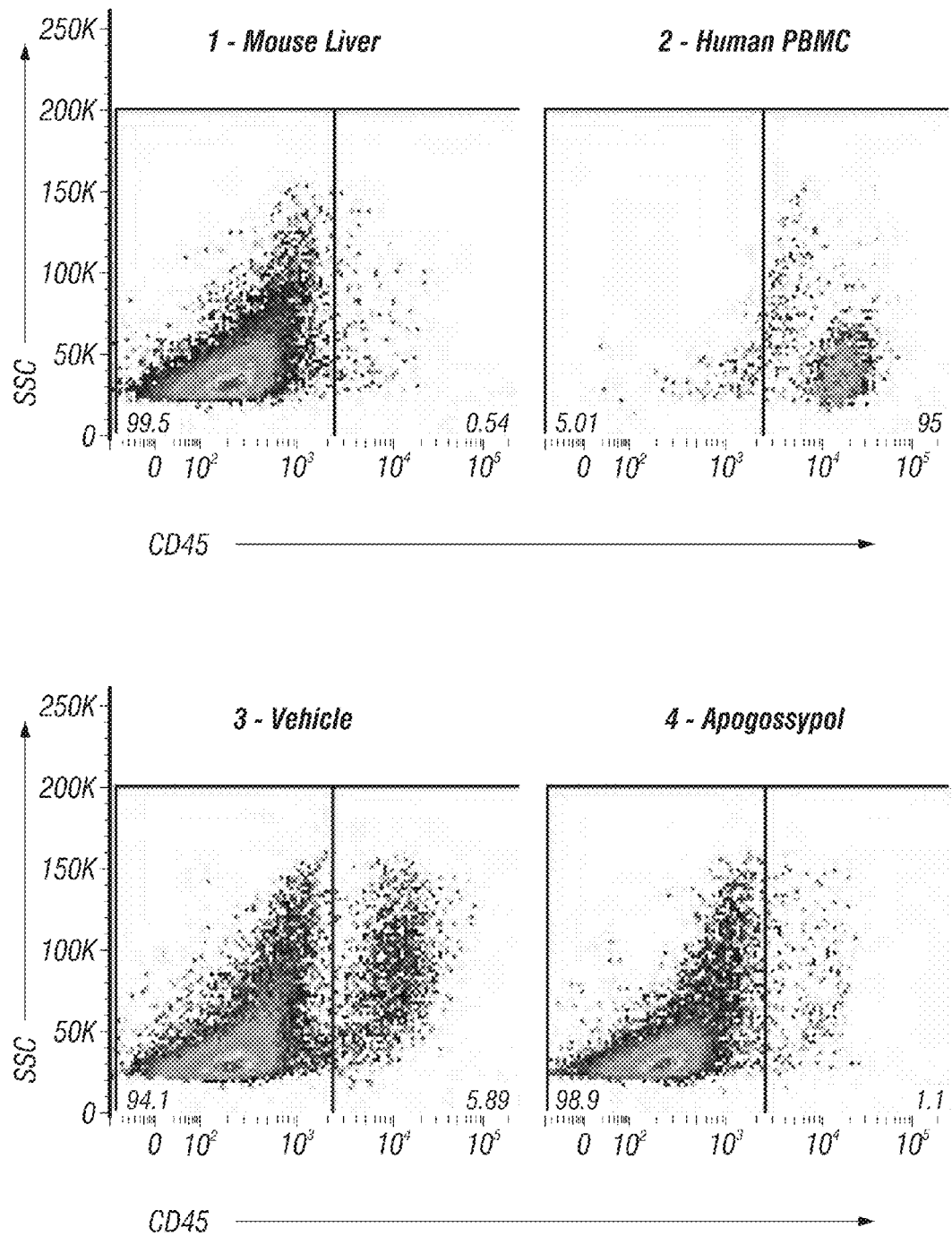
FIG. 4B illustrates a representative FACS data of CD45+ cells in mouse livers transplanted with progenitors (CD34+CD38+Lin−) from CML BC-derived tumors.

FIG. 4B. Representative FACS data of CD45$^+$ cells in mouse livers transplanted with progenitors (CD34$^+$CD38$^+$Lin$^-$) from CML BC-derived tumors. Transplanted mice were treated by oral gavage daily for 3 weeks starting at 10 weeks post-transplant with 120 µg/kg apogossypol or vehicle. Mouse livers were harvested at 13 weeks post-transplant, stained, and analyzed for human CD45$^+$ cells using FACS.

Figure 4C:
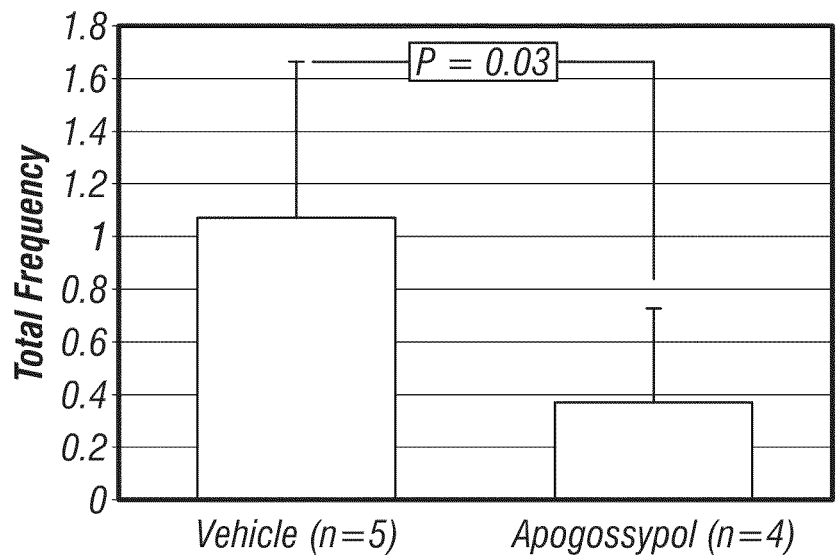
FIG. 4C illustrates a FACS analysis of the average overall frequency of human CD45+ cells in transplanted mouse livers after treatment with apogossypol (n=4) or vehicle (n=5)

FIG. 4C. FACS analysis of the average overall frequency of human CD45$^+$ cells in transplanted mouse livers after treatment with apogossypol (n=4) or vehicle (n=5) demonstrates a statistically significant (p=0.03) decrease in tumor cell engraftment after 3 weeks of apogossypol treatment.

Figure 4D:
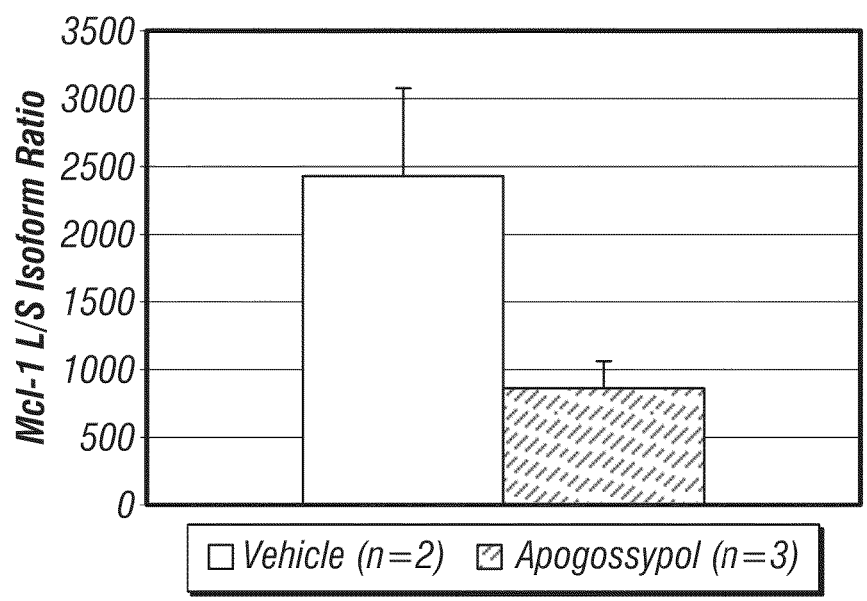
FIG. 4D illustrates analysis of a Mcl-1 long and short isoform levels by qPCR (see FIG. 3) in tumor cells harvested from mice treated with apogossypol (n=3) or vehicle (n=2); as described in detail in Example 1, below.
Figure 5:
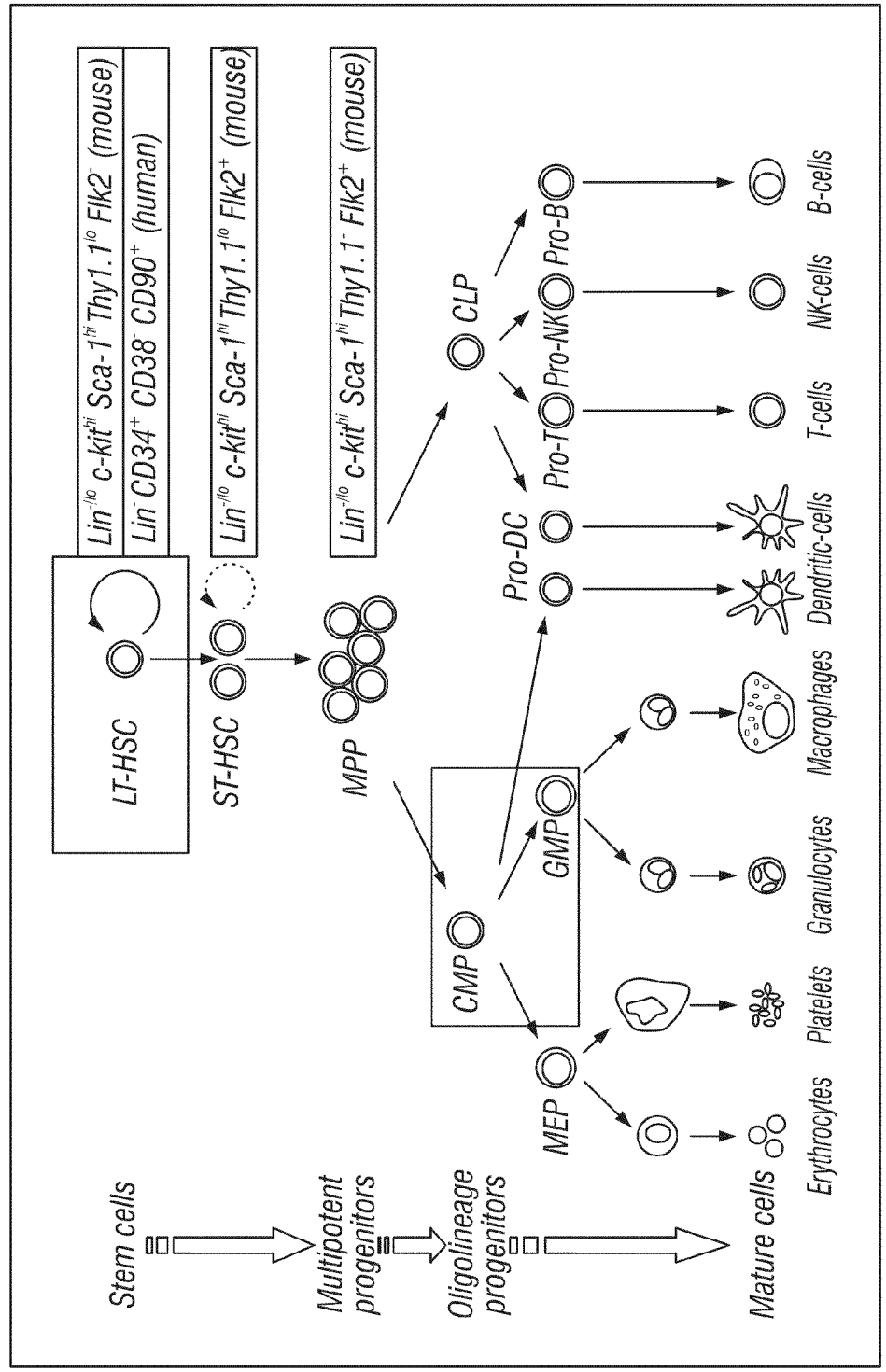
FIG. 5 illustrates MyeloProliferative Neoplasm (MPN) progression, and the progression of stem cells to multipotent progenitors, oligolineage progenitors and to mature cells, and genes associated with these cell maturations.
Figure 6:
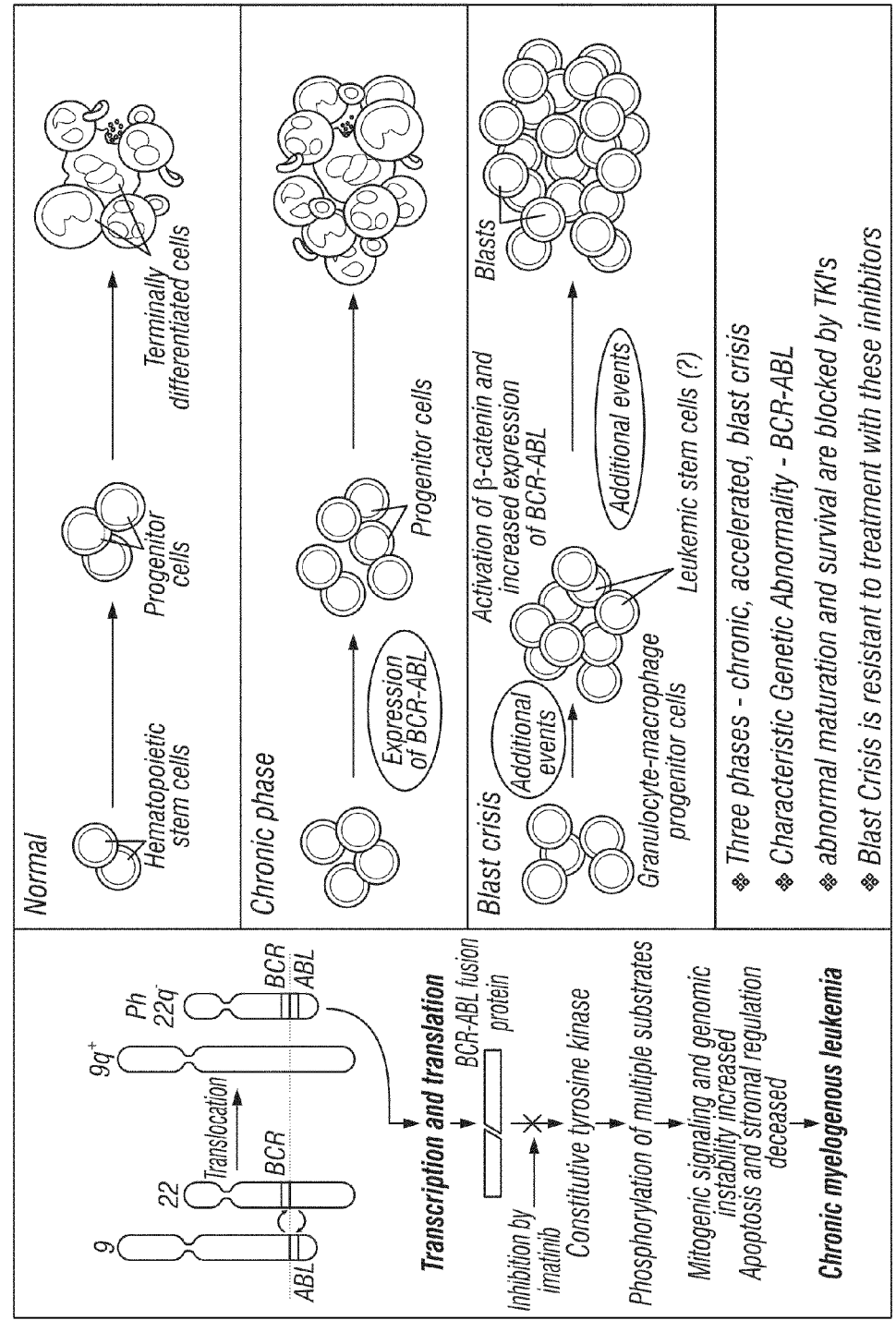
FIG. 6 illustrates stem and progenitor cell hierarchies in chronic myeloid leukemia (CML), including the three phases: chronic, accelerated and blast crisis.
Figure 7:
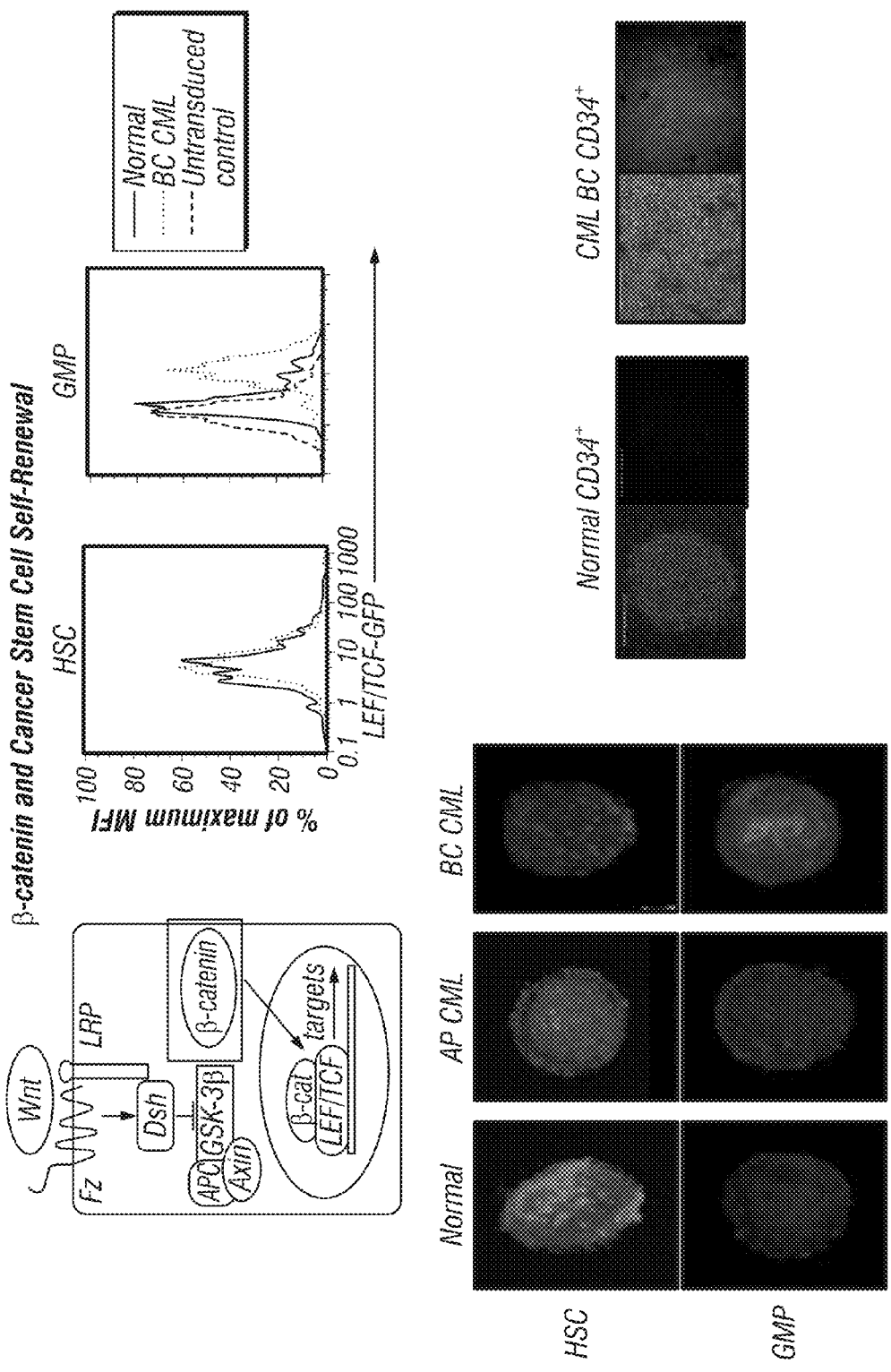
FIG. 7 illustrates β-catenin and cancer stem cell self-renewal pathways.
Figure 8:
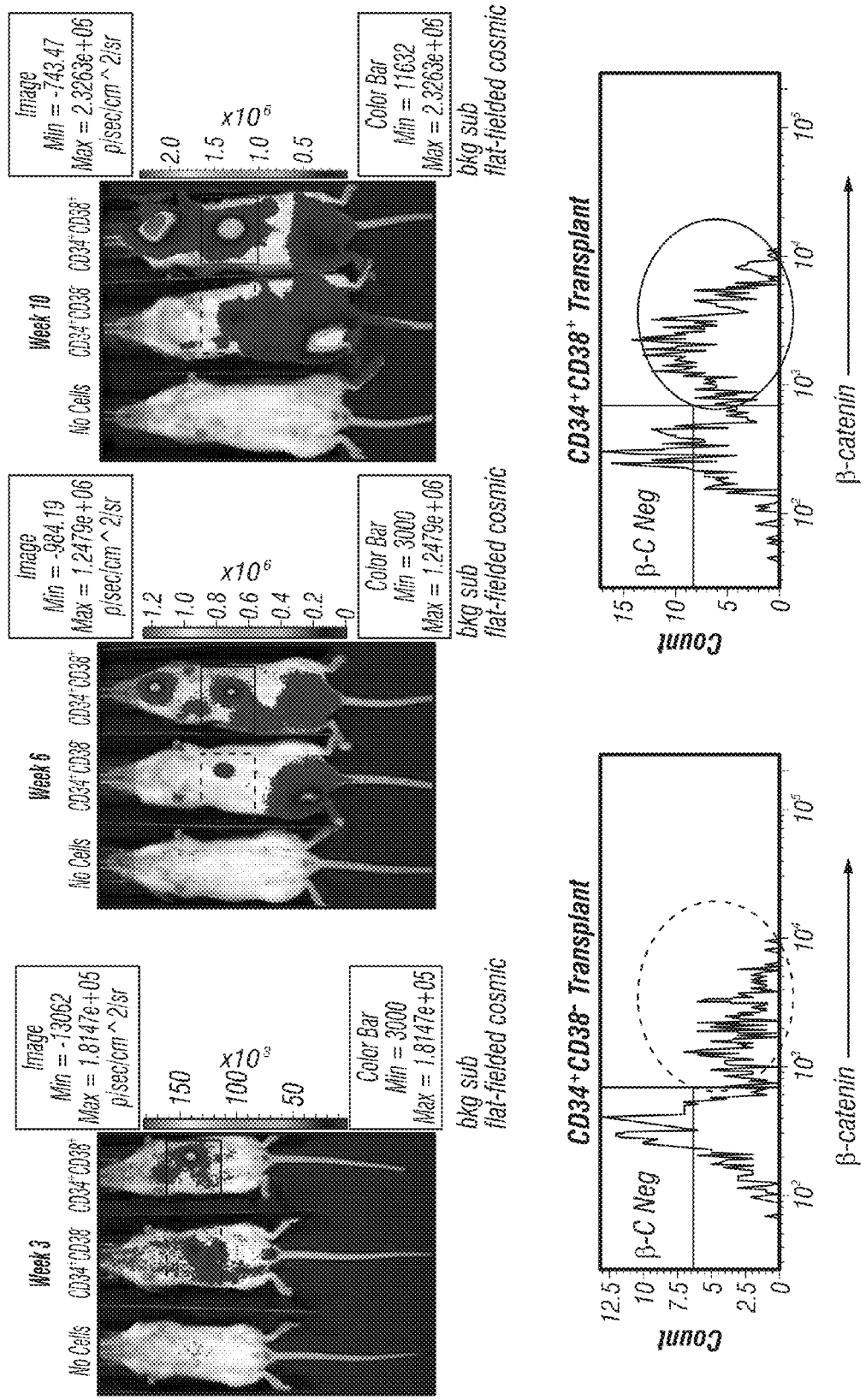
FIG. 8, FIG. 9 and FIG. 10 illustrate data demonstrating that glycogen synthase kinase 3β missplicing contributes to leukemia stem cell generation.
Figure 9:
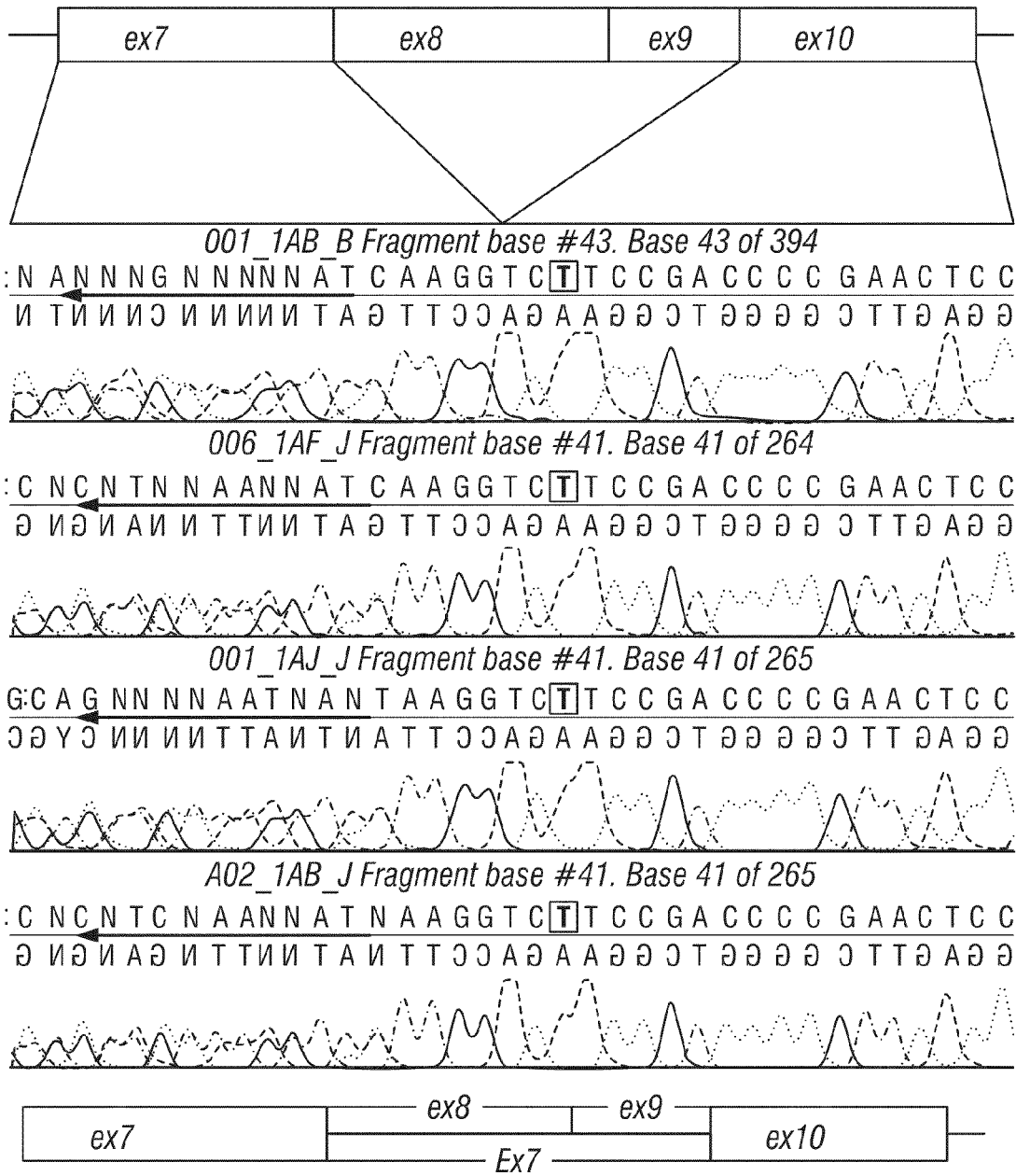
Figure 10:
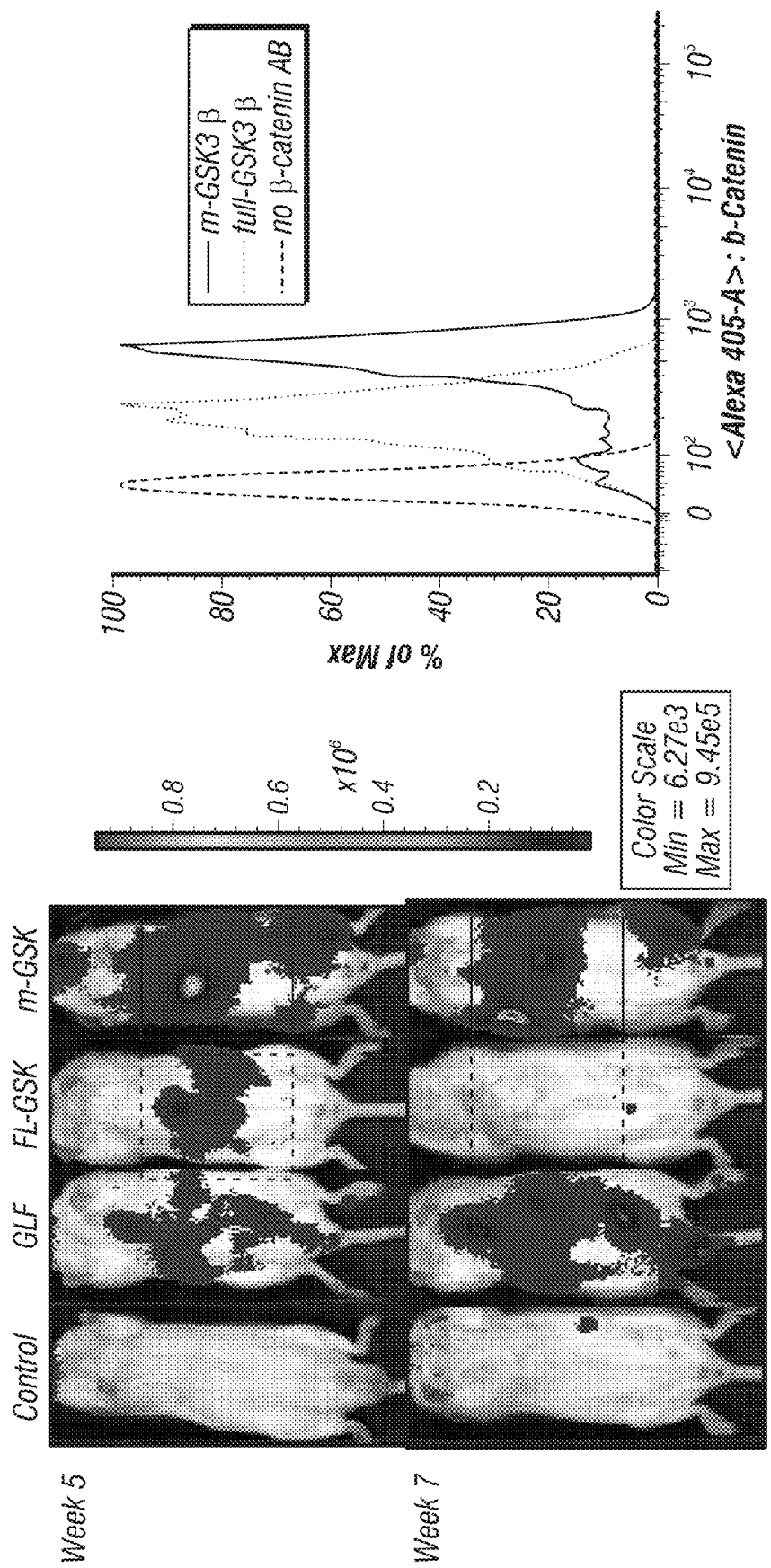
Figure 11:
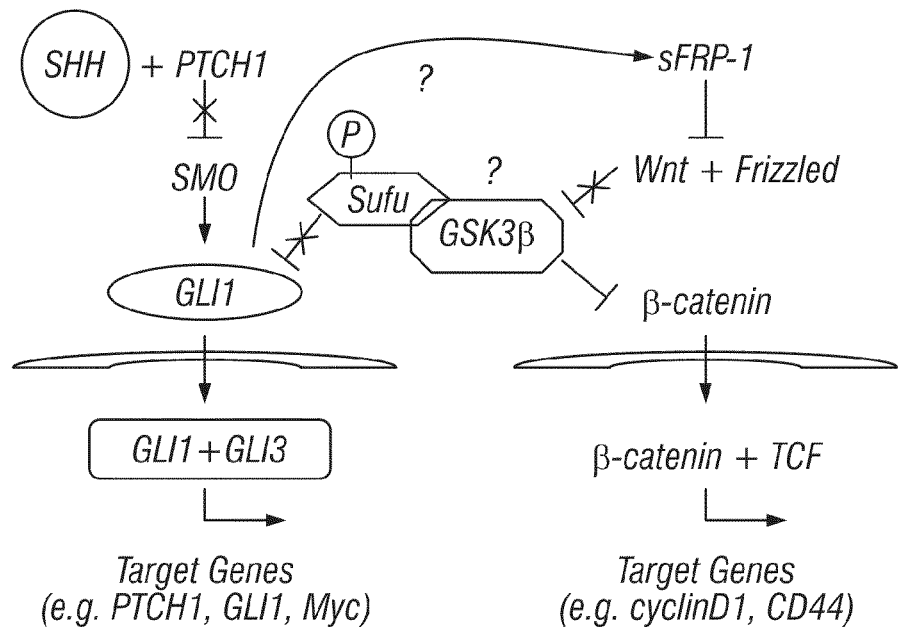
FIG. 11 illustrates a proposed cross-talk between SHH and WNT pathways in CML; the invention is not limited by any particular mechanism of action.
Figure 12:
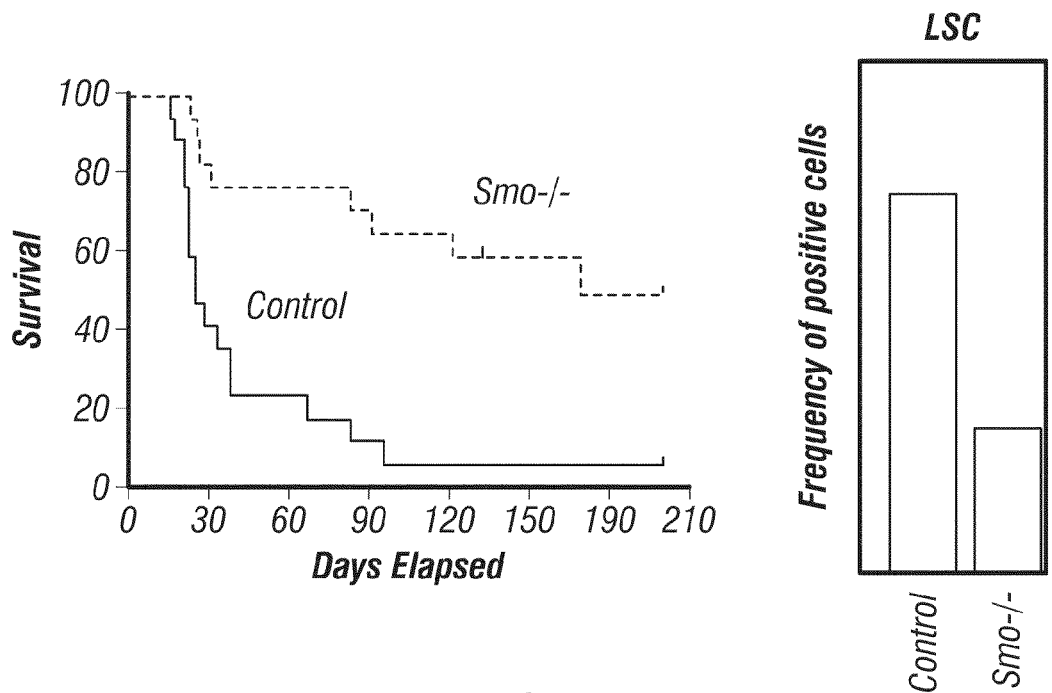
FIG. 12 and FIG. 13 illustrate data demonstrating that hedgehog signaling is essential for maintenance of cancer stem cells in myeloid leukemia.
Figure 13:
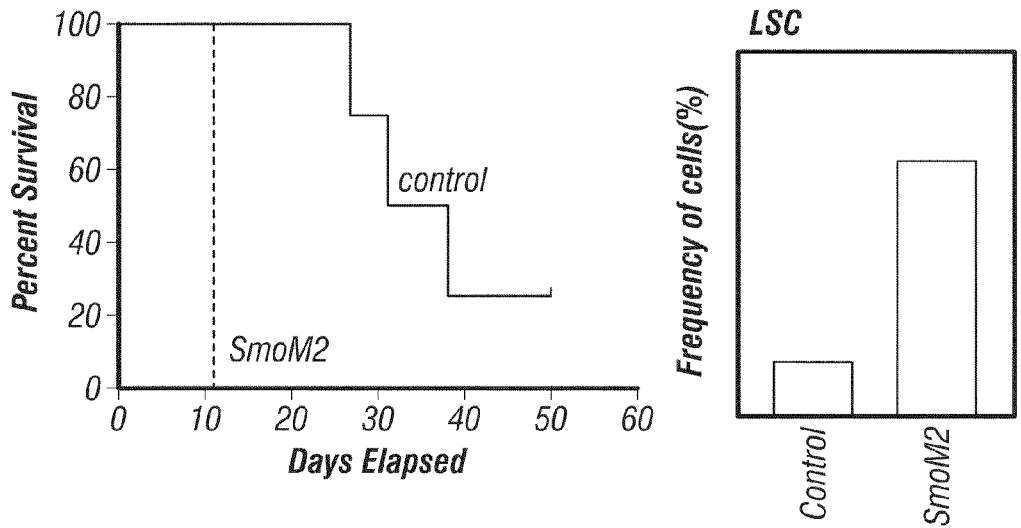
Figure 14:
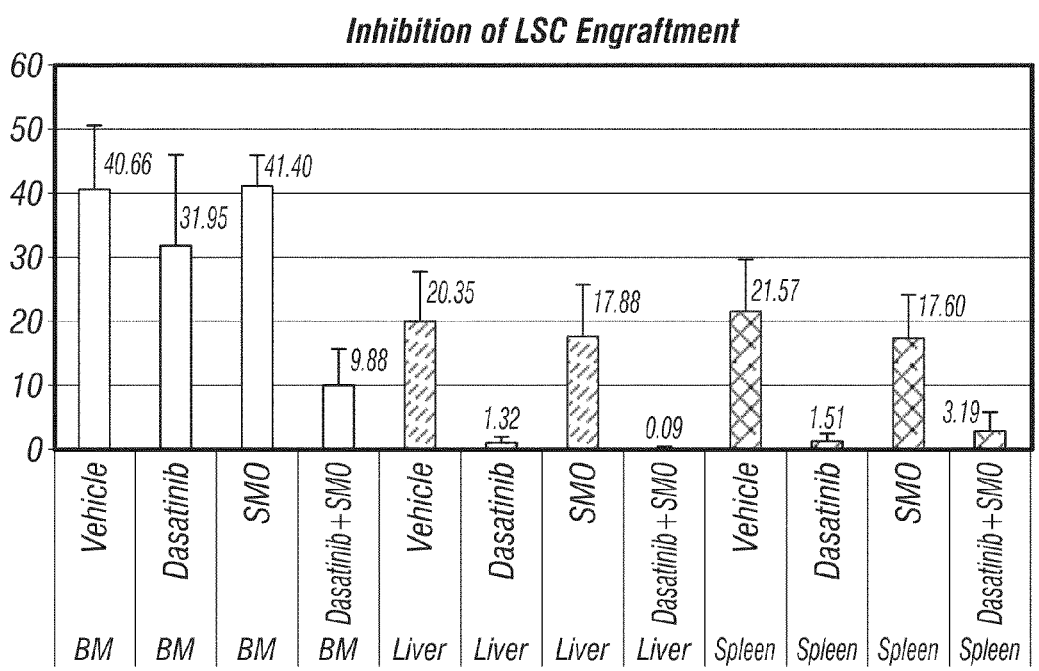
FIG. 14 illustrates data demonstrating inhibition of Leukemic Stem Cell (LSC) engraftment using various compounds, as illustrated in the figure.
Figure 15:
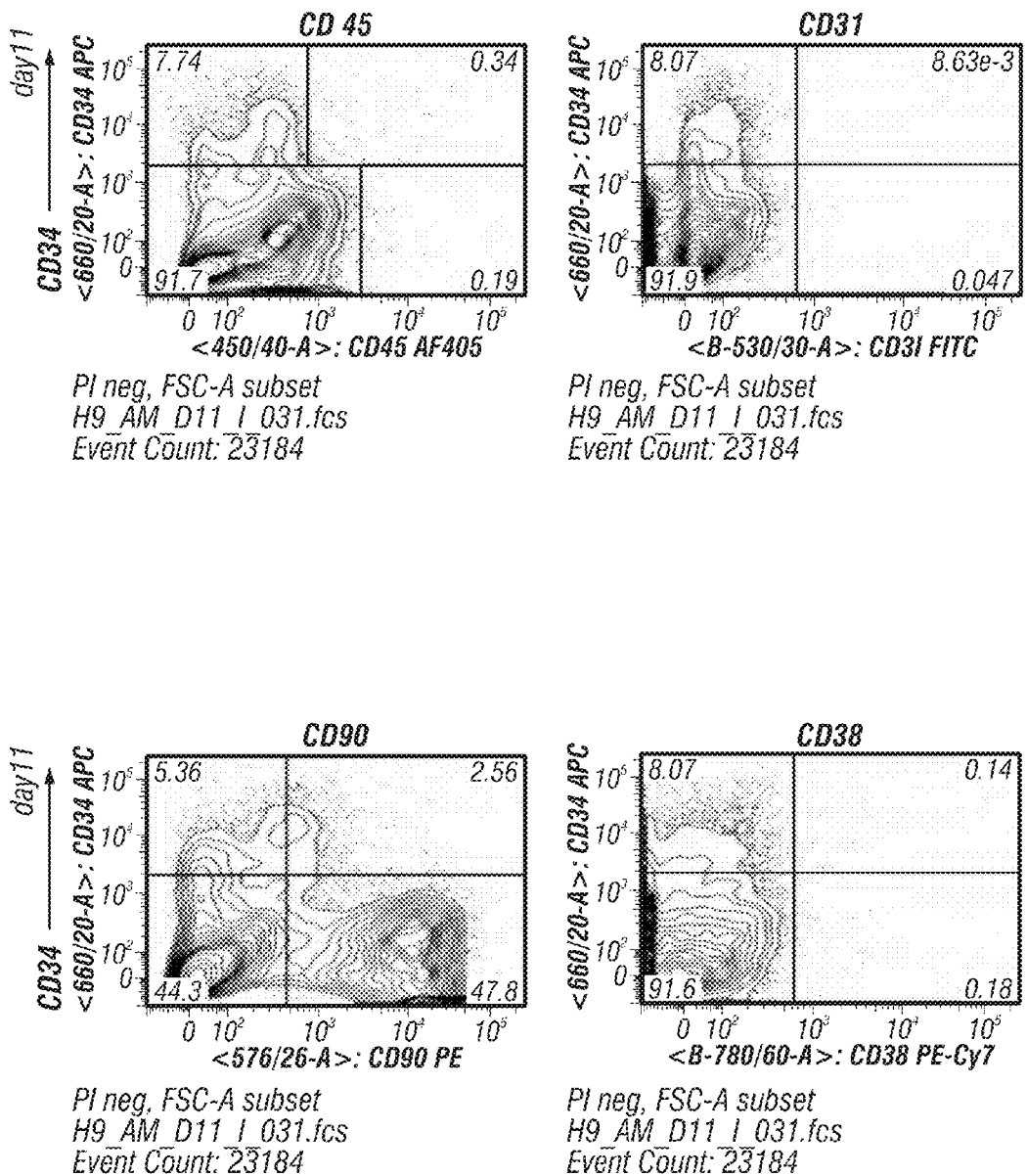
FIG. 15 illustrates data demonstrating generation of CML LSC from human embryonic stem cells (hESC).
Figure 16A:
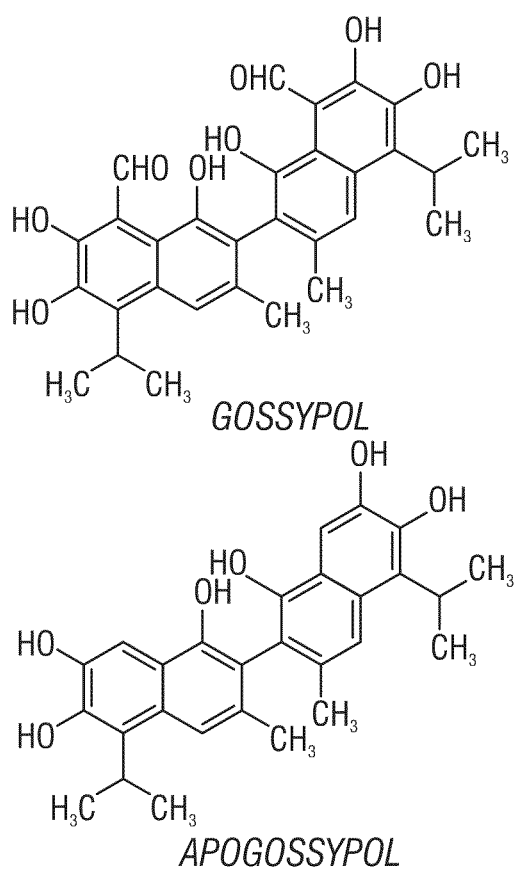
FIG. 16 illustrates data demonstrating targeted inhibition of LSC survival using gossypol compounds.
Figure 16B:
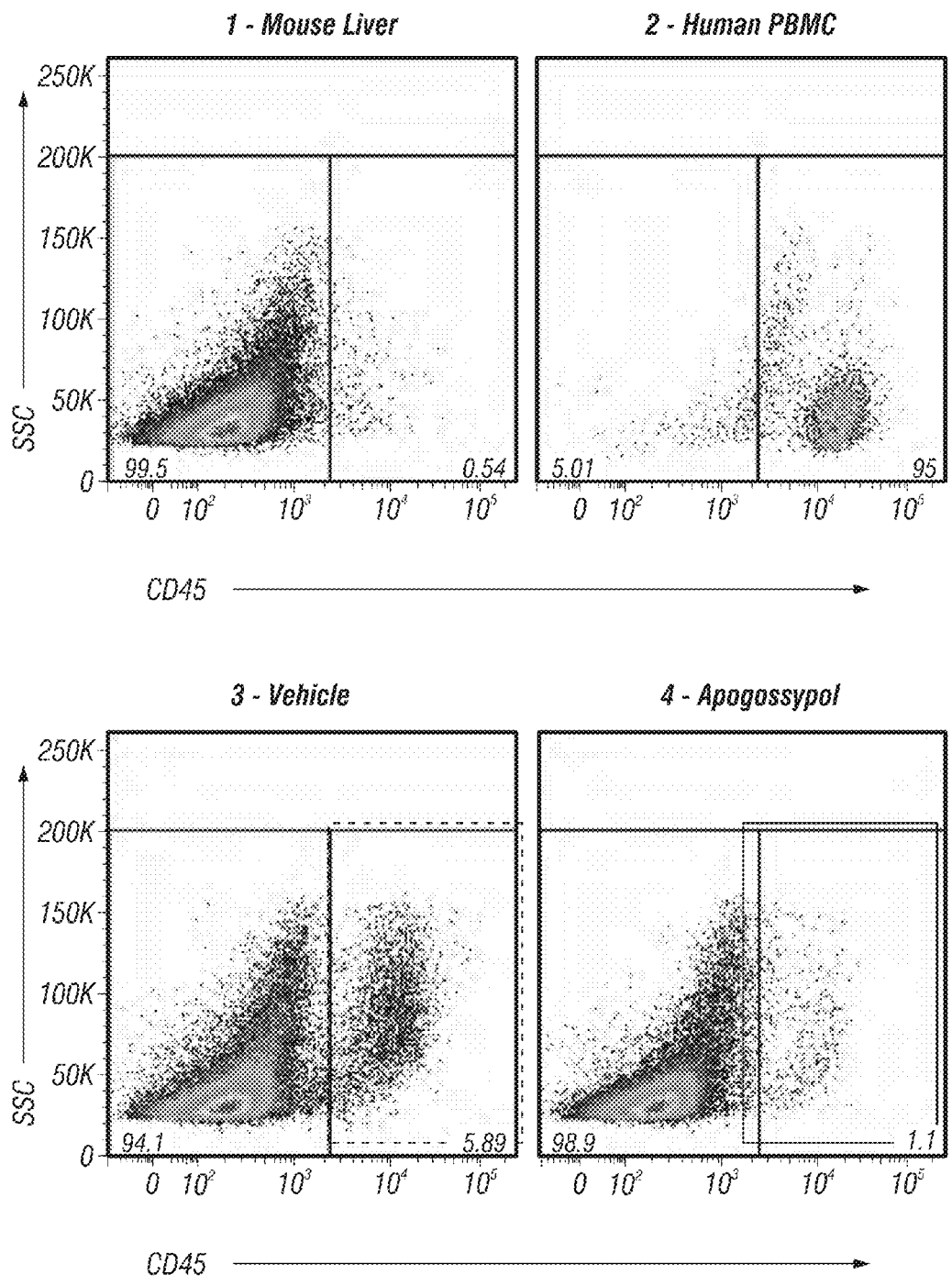
Figure 16C:
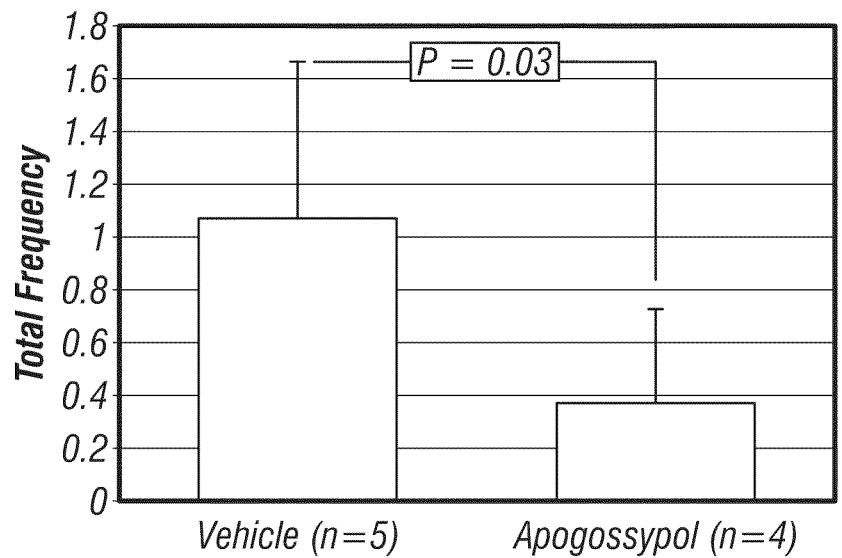
Figure 16D:
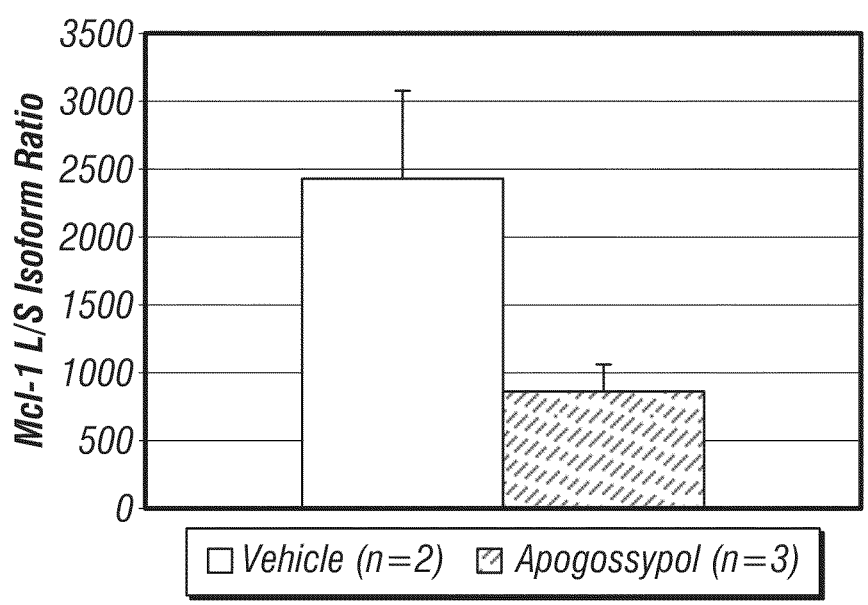
Figure 17:
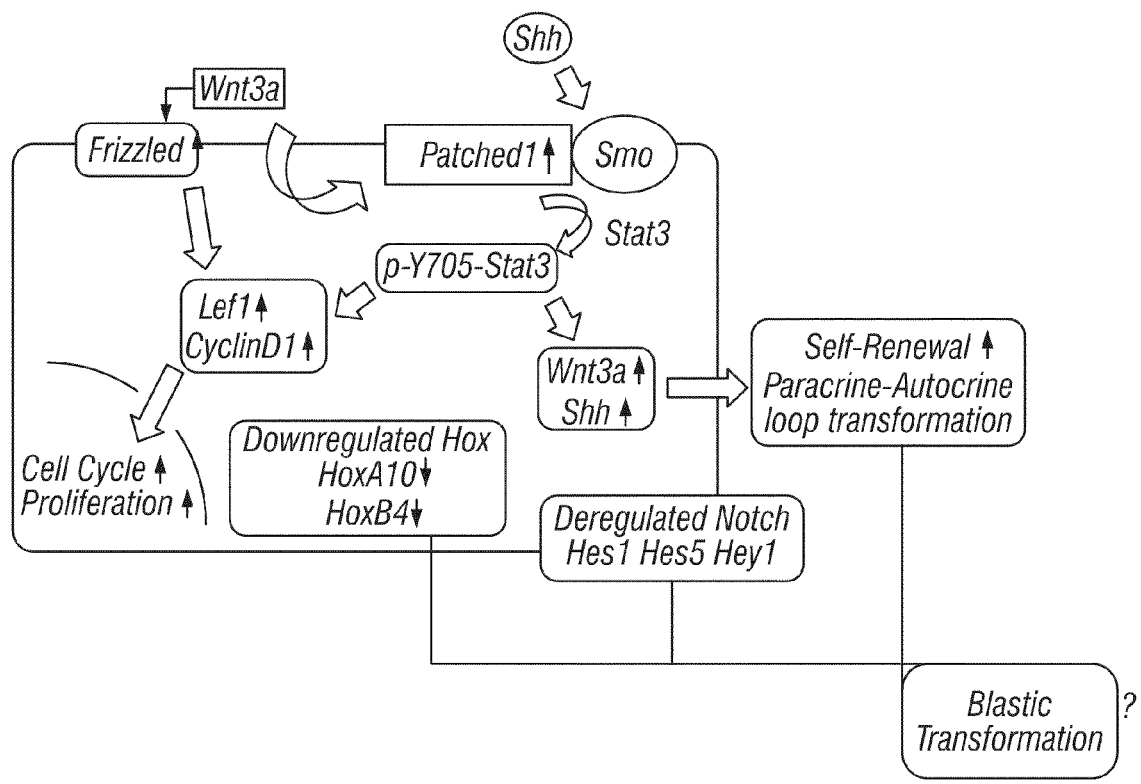
FIG. 17 illustrates self-renewal pathway cross-talk, including self-renewal paracrine-autocrine loop transformation and blastic transformation; the invention is not limited by any particular mechanism of action.
Figure 18:
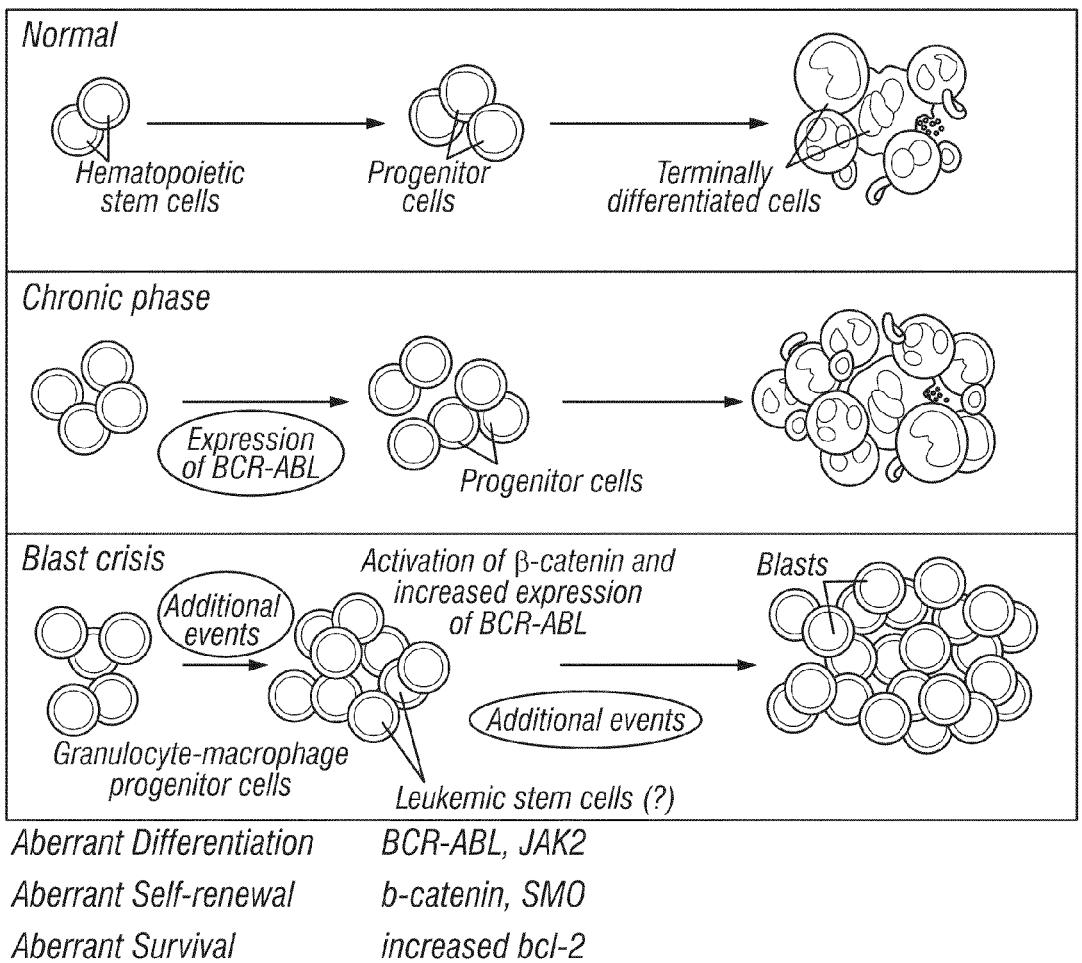
FIG. 18 illustrates a model of molecular evolution of LSCs, including aberrant differentiation (BCR-ABL, JAK2), aberrant self-renewal (β-catenin, SMO), and aberrant survival (increased bcl-1); the invention is not limited by any particular mechanism of action.
Figure 19:
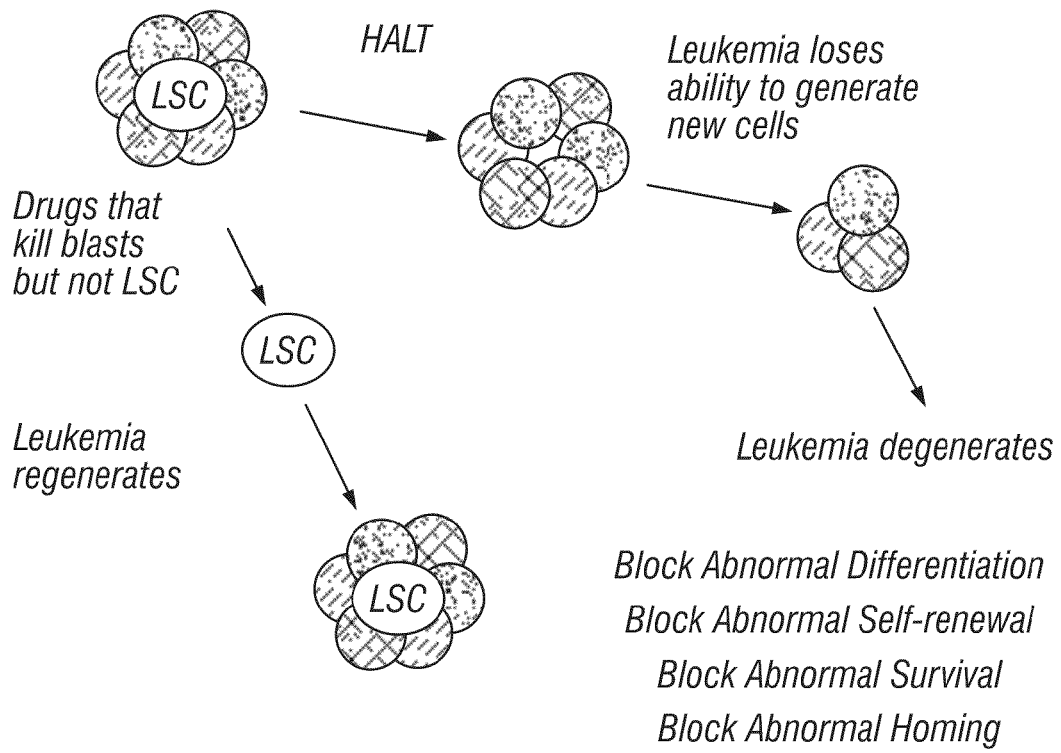
FIG. 19 illustrates an exemplary scheme for highly active anti-leukemic stem cell therapy (HALT); the invention is not limited by any particular mechanism of action Like reference symbols in the various drawings indicate like elements.

FIG. 4D. While the invention is not limited by any particular mechanism of action, this figure illustrates a possible novel mechanism of apogossypol inhibition of CML tumor cells. Mcl-1 long and short isoform levels were analyzed by qPCR (see FIG. 3) in tumor cells harvested from mice treated with apogossypol (n=3) or vehicle (n=2). Tumor cells exposed to apogossypol had higher Mcl-1 short isoform expression (not shown) and thus a lower Mcl-1 long/short isoform ratio then vehicle treated cells.

CONCLUSIONS

CML cancer stem cells deregulate apoptosis by over-expression of Bcl-2 and by aberrant expression of Mcl-1. Targeting these abnormalities using compounds such as Apogossypol can inhibit the engraftment of these cells and can be a useful therapeutic approach for treating leukemia.

REFERENCES

1. Jamieson et al, NEJM 2004; 351:6576-67.
2. Traggiai et al, Science 2004 Apr. 2; 304(5667):104-7
3. Jaiswal et al, PNAS 2003; 100(17):10002-7
4. Radich et al, PNAS 2006; 103(8):2794-9
5. Sanchez-Garcia et al, PNAS 1995; 92(12):5287-91
6. Gorre et al, Science 2001; 293(5531):876-80
7. Geron et al, Cancer Cell 2008; 13(4):321-30
8. Kitada et al, Blood 2007; 111(6):3211-9.
9. Akgul et al, CMLS 2004; 61:2189-99

A number of embodiments of the invention have been described. Nevertheless, it will be understood that various modifications may be made without departing from the spirit and scope of the invention. Accordingly, other embodiments are within the scope of the following claims.

What is claimed is:

1. A method for increasing the susceptibility of a CD34+CD38+lin− cell to apoptosis comprising:
   (a) isolating CD34+CD38+lin− CML cells from the blood or bone marrow of a patient with chronic myeloid leukemia; and
   (b) contacting the isolated CD34+CD38+lin− CML cells with apogossypol,
   wherein contact of the apogossypol with the CD34+CD38+lin− CML cells causes an increase in the expression of a short isoform of a myeloid cell leukemia sequence 1 transcript (Mcl-1) in the CML cells, and a lower ratio of the Mcl-1 long isoform to the Mcl-1 short isoform, thereby increasing the susceptibility of a CD34+CD38+lin− cell to apoptosis.

* * * * *